(12) United States Patent
Watts et al.

(10) Patent No.: US 10,689,353 B2
(45) Date of Patent: Jun. 23, 2020

(54) METHOD FOR THE MANUFACTURE OF EFAVIRENZ

(71) Applicant: NELSON MANDELA METROPOLITAN UNIVERSITY, Port Elizabeth (ZA)

(72) Inventors: Paul Watts, Port Elizabeth (ZA); Sravanthi Chada, Port Elizabeth (ZA)

(73) Assignee: NELSON MANDELA METROPOLITAN UNIVERSITY, Port Elizabeth (ZA)

( * ) Notice: Subject to any disclaimer, the term of this patent is extended or adjusted under 35 U.S.C. 154(b) by 0 days.

(21) Appl. No.: 16/488,975

(22) PCT Filed: Feb. 15, 2018

(86) PCT No.: PCT/IB2018/050916
§ 371 (c)(1),
(2) Date: Aug. 27, 2019

(87) PCT Pub. No.: WO2018/154414
PCT Pub. Date: Aug. 30, 2018

(65) Prior Publication Data
US 2020/0062722 A1  Feb. 27, 2020

(30) Foreign Application Priority Data
Feb. 23, 2017  (NL) .................. 2018412

(51) Int. Cl.
*C07D 263/58* (2006.01)
(52) U.S. Cl.
CPC .................. *C07D 263/58* (2013.01)
(58) Field of Classification Search
CPC .................. C07D 263/58

USPC .................. 544/92
See application file for complete search history.

(56) References Cited

U.S. PATENT DOCUMENTS 6,147,210 A  11/2000  Pierce et al.

FOREIGN PATENT DOCUMENTS

WO  9851676 A1  11/1998

OTHER PUBLICATIONS

Radesca et al. Synthetic Communications, vol. 27, No. 24, Jun. 17, 1997, pp. 4373-4384.*
International Search Report and Written Opinion Form PCT/ISA/210 and PCT/ISA/237, International Application No. PCT/IB2018/050916, pp. 1-9, International Filing Date Feb. 15, 2018, dated May 16, 2018.
Radesca L. et al: "Synthesis of HIV-1 reverse transcriptase inhibitor DMP 266", Synthetic Communications, vol. 27, No. 24, Jun. 17, 1997 (Jun. 17, 1997), pp. 4373-4384, XP002779484, scheme 1.
Correia C et al: "A concise flow synthesis of Efavirenz", Angew. Chem. Int. Ed., vol. 54, Feb. 27, 2015 (Feb. 27, 2015), pp. 4945-4948, XP002779485, cited in the application Schemes 3 and 4.

* cited by examiner

*Primary Examiner* — Kahsay Habte
(74) *Attorney, Agent, or Firm* — Bond Schoeneck & King, PLLC; George McGuire

(57) ABSTRACT

This invention relates to a method for the manufacture of optically pure (S)-6-chloro-(cyclopropylethynyl)-1,4-dihydro-4-(trifluoromethyl)-2H-3,1-benzoxazin-2-one. Specifically, this invention relates to a flow synthesis method for the manufacture of (S)-6-chloro-(cyclopropylethynyl)-1,4-dihydro-4-(trifluoromethyl)-2H-3,1-benzoxazin-2-one.

25 Claims, 10 Drawing Sheets

METHOD FOR THE MANUFACTURE OF EFAVIRENZ

CROSS REFERENCE TO RELATED APPLICATIONS

This application is a U.S. National Phase Application of International Patent Application number PCT/IB2018/050916 filed on 15 Feb. 2018, which claims the priority to the Netherlands Application No. 2018412 filed on 23 Feb. 2017, the disclosures of both of which are incorporated herein by reference in their entireties.

INTRODUCTION

This invention relates to a method for the manufacture of optically pure (S)-6-chloro-(cyclopropylethynyl)-1,4-dihydro-4-(trifluoromethyl)-2H-3,1-benzoxazin-2-one. In particular, but not exclusively, the invention relates to a flow synthesis method for the manufacture of (S)-6-chloro-(cyclopropylethynyl)-1,4-dihydro-4-(trifluoromethyl)-2H-3,1-benzoxazin-2-one.

BACKGROUND

Efavirenz is an active pharmaceutical ingredient used in the manufacture of medicaments for the treatment and prevention of HIV/AIDS. Efavirenz is chemically described as (S)-6-chloro-(cyclopropylethynyl)-1,4-dihydro-4-(trifluoromethyl)-2H-3,1-benzoxazin-2-one. It is generally recommended for use with other antiretrovirals, for example in combination with Emtricitabine, Lamivudine, and/or Tenofovir. Efavirenz is listed on the World Health Organization's List of Essential Medicines, the most effective and safe medicines needed in a health system.

There are numerous processes and synthetic routes described in the prior art for the preparation of Efavirenz. However, existing synthesis methodologies for the production of these compounds have essentially been based on standard stirred batch or bench top reactor type processes which utilize significant volumes of organic solvents. These processes have its limits, including inefficient temperature and pressure controls as well as the inability to handle hazardous reagents safely. The application of continuous flow microreactors, or micro reactor technology, to reaction chemistries such as this one, could provide a potential practical solution that could be used to overcome some of these drawbacks.

In addition, Efavirenz has a stereogenic quaternary carbon center bearing a trifluoromethyl group with the (S) configuration. Biological evaluation of optically active Efavirenz has revealed that the (R) enantiomer exhibits virtually no activity. Therefore, establishment of the quaternary carbon center with the (S) configuration in an asymmetric manner is one of the main challenges for the synthesis of Efavirenz.

Correia et al., *Angew. Chem. Int. Ed.* 2015, 54, 4945-4948 discloses a method for the flow synthesis preparation of Efavirenz. The disclosure relates to a five step process for the synthesis of a racemic mixture of Efavirenz with an overall yield of 45% rac-Efavirenz.

There is therefore a need for an improved method for the manufacture of Efavirenz. In particular, there is a need for a method for the manufacture of the (S) enantiomer of Efavirenz, the method preferably being a flow synthesis method. The present invention seeks to address some of the shortcomings of the prior art by providing new methods for the manufacture of optically pure Efavirenz.

SUMMARY OF THE INVENTION

According to a first aspect of the present invention there is provided a method for the manufacture of (S)-6-chloro-(cyclopropylethynyl)-1,4-dihydro-4-(trifluoromethyl)-2H-3,1-benzoxazin-2-one of formula 8

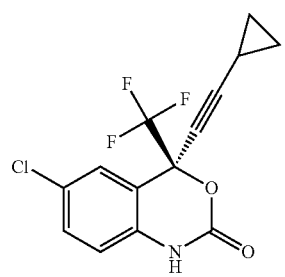

comprising the steps of:
a) preparing tert-butyl-4-chloro phenyl carbamate of formula 26

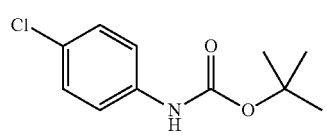

by reacting 4-chloroaniline with di-tert-butyl dicarbamate, b) reacting the tert-butyl-4-chloro phenyl carbamate of formula 26 with butyllithium and piperidine trifluoroacetic acid of formula 67

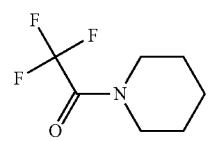

in a trifluroacetylation reaction to produce tert-butyl-4-chloro-2-(2,2,2-trifluoroacetyl) phenyl carbamate of formula 27

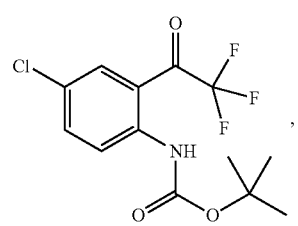

c) reacting the compound of formula 27 with cyclopropyl acetylene of formula 53 and (1R,2S) N-pyrrolidinyl-norephedrine of formula 60

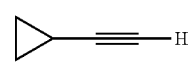

-continued

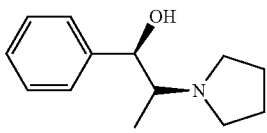

60 in the presence of butyllithium to produce (S)-2-(2-amino-5-chlorophenyl)-4-cyclopropyl-1,1,1-trifluoro-3-butyn-2-ol of formula 56

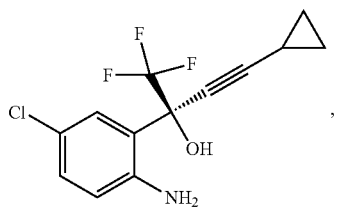

56 d) reacting the compound of formula 56 with a compound of the formula 70

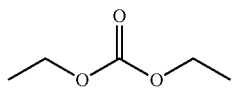

70 in the presence of 1,8-diazabicyclo[5.4.0]undec-7-ene to produce (S)-6-chloro-(cyclopropylethynyl)-1,4-dihydro-4-(trifluoromethyl)-2H-3,1-benzoxazin-2-one of formula 8, wherein the method is a flow synthesis method.

Preferably, the method is a semi-continuous flow synthesis method.

In one embodiment the butyllithium in step (b) or step (c) is n-butyllithium.

Preferably, in step (b) the reaction is performed in the presence of tetramethylethylenediamine.

In a preferred embodiment the reactions of steps (a)-(d) are each independently performed in a solvent or solvent mixture selected from the group consisting of tetrahydrofuran, dichloromethane, acetonitrile, acetone, water, and mixtures thereof.

The method may further comprise the step of recrystallization from a solution of ethyl acetate in heptane.

According to a second aspect of the present invention there is provided a method for the manufacture of (S)-6-chloro-(cyclopropylethynyl)-1,4-dihydro-4-(trifluoromethyl)-2H-3,1-benzoxazin-2-one of formula 8

8

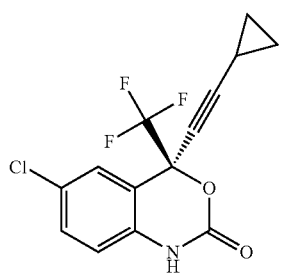

comprising the steps of:

a) preparing tert-butyl-4-chloro phenyl carbamate of formula 26

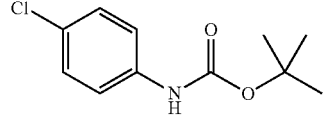

26 by reacting 4-chloroaniline with di-tert-butyl dicarbamate, b) reacting the tert-butyl-4-chloro phenyl carbamate of formula 26 with cyclopropylethynyl trifluoromethyl ketone of formula 29 and (1R,2S) N-pyrrolidinyl-norephedrine of formula 60

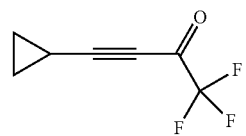

29

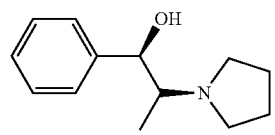

60 in the presence of butyllithium to produce (S)-2-(2-amino-5-chlorophenyl)-4-cyclopropyl-1,1,1-trifluoro-3-butyn-2-ol of formula 56

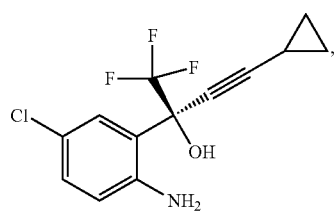

56 c) reacting the compound of formula 56 with a compound of the formula 70

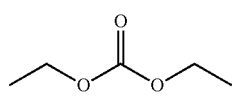

70 in the presence of 1,8-diazabicyclo[5.4.0]undec-7-ene to produce (S)-6-chloro-(cyclopropylethynyl)-1,4-dihydro-4-(trifluoromethyl)-2H-3,1-benzoxazin-2-one of formula 8, wherein the method is a flow synthesis method.

Preferably, the method is a semi-continuous flow synthesis method.

In one embodiment, the butyllithium in step (b) is n-butyllithium.

In a preferred embodiment, the reactions of steps (a)-(c) are each independently performed in a solvent or solvent mixture selected from the group consisting of tetrahyroduran, dichloromethane, acetonitrile, acetone, water, and mixtures thereof.

The method may further comprise the step of recrystallization from a solution of ethyl acetate in heptane.

In a preferred embodiment the reaction of step (a) has a residence time of between about 5 minutes and about 12 minutes.

Preferably, in step (a) the molar ratio of 4-chloroaniline to di-tert-butyl dicarbamate is in the range of about 1:1 to 1:1.2.

Preferably the reaction of step (a) is performed at a temperature of about 30° C. to about 60° C.

In one embodiment the reaction of step (b) is performed at a temperature of about −60° C. to about −40° C.

The reaction of step (b) may have a residence time of between about 5 minutes and about 12 minutes.

In a preferred embodiment, in step (c) the molar ratio of tert-butyl-4-chloro-2-(2,2,2-trifluoroacetyl) phenyl carbamate of formula 27 to cyclopropyl acetylene of formula 53 is in the range of about 1:1.2 to 1:1.4.

Preferably, the reaction of step (d) or (c) respectively has a residence time of between about 2 minutes and about 10 minutes.

In one embodiment the reaction of step (d) or (c) respectively is performed at a temperature of about 80° C. to 120° C.

Preferably, in step (d) or (c) respectively the molar ratio of (S)-2-(2-amino-5-chlorophenyl)-4-cyclopropyl-1,1,1-trifluoro-3-butyn-2-ol of formula 56 to compound of the formula 70 is in the range of about 1:1.1 to 1:1.4.

BRIEF DESCRIPTION OF THE DRAWINGS

The invention will now be described in more detail with reference to the following non-limiting embodiments and figures in which.

DETAILED DESCRIPTION OF A PREFERRED EMBODIMENT

The present invention will now be described more fully hereinafter with reference to the accompanying figures, in which some of the non-limiting embodiments of the invention are shown.

The invention as described hereinafter should not be construed to be limited to the specific embodiments disclosed, with slight modifications and other embodiments intended to be included within the scope of the invention.

Although specific terms are employed herein, they are used in a generic and descriptive sense only and not for purposes of limitation.

As used herein, throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having", "including", and variations thereof used herein, are meant to encompass the items listed thereafter, and equivalents thereof as well as additional items.

The present invention provides for a method for the manufacture of optically pure (S)-6-chloro-(cyclopropylethynyl)-1,4-dihydro-4-(trifluoromethyl)-2H-3,1-benzoxazin-2-one. In particular, but not exclusively, the invention relates to a semi-continuous flow synthesis method for the manufacture of (S)-6-chloro-(cyclopropylethynyl)-1,4-dihydro-4-(trifluoromethyl)-2H-3,1-benzoxazin-2-one.

Where used in this specification, unless the context indicates otherwise, the term "flow synthesis" should be understood to mean that all steps of a particular (multi-step) chemical synthesis are run in a continuously flowing stream rather than in batch production. In other words, pumps move fluid into a tube (or reactor), and where tubes join one another, the fluids contact one another. If these fluids are reactive, a reaction takes place.

Where used in this specification, unless the context indicates otherwise, the term "semi-continuous flow synthesis" should be understood to mean that an intermediate is isolated between steps rather than flowing directly into the next step of the continuous process.

Figure 1:
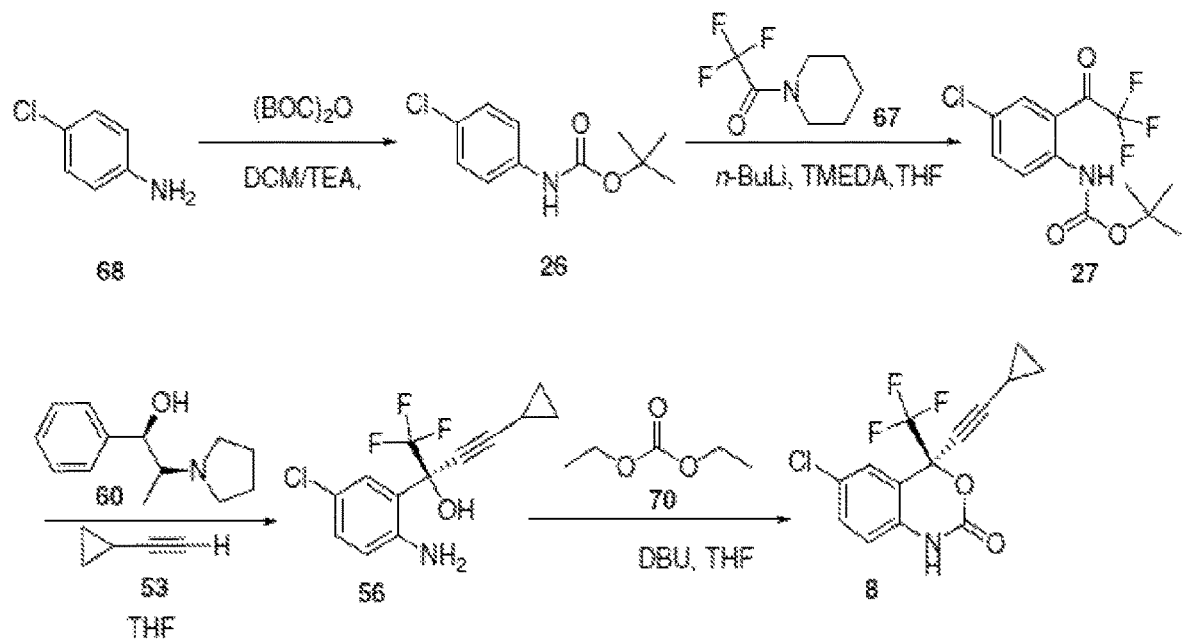
FIG. 1 shows a schematic representation of a general synthesis method of the invention.
Figure 2:
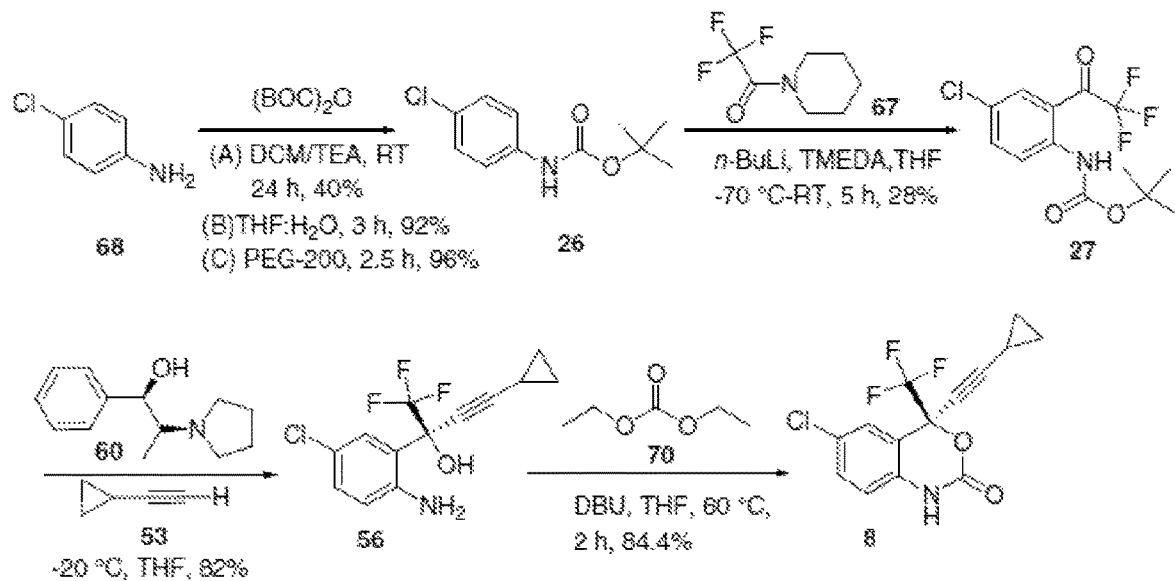
FIG. 2 shows a schematic representation of the batch synthesis process according to the invention.
Figure 3:
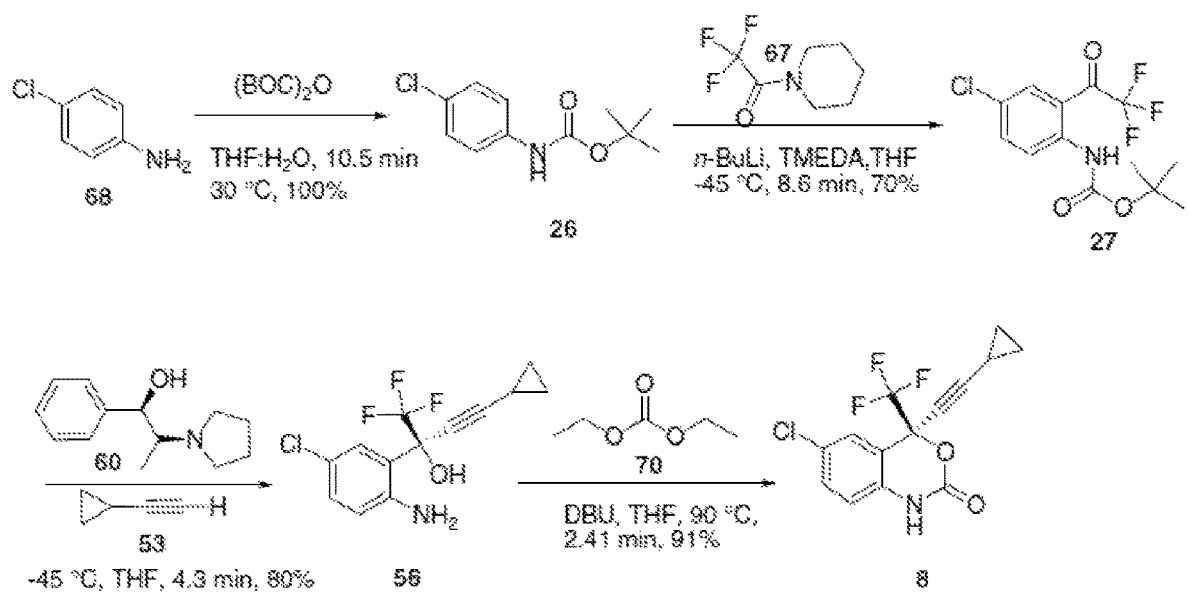
FIG. 3 shows a schematic representation of the flow synthesis process according to the invention.

FIG. 1 shows a schematic representation of the general synthesis method and synthesis steps of one embodiment of the invention for making chiral (S)-6-chloro-(cyclopropylethynyl)-1,4-dihydro-4-(trifluoromethyl)-2H-3,1-benzoxazin-2-one, also known as efavirenz. FIG. 2 and FIG. 3 shows specific schematic representations of the batch process and the semi continuous flow synthesis method, according to the invention, respectively.

The inventors have shown that method of the present invention can be performed using either conventional batch chemistry techniques or more advanced semi continuous flow synthesis methods. It will be appreciated by those skilled in the art that while even a batch method to produce optically pure efavirenz would be highly desired, a method for producing optically pure efavirenz in semi continuous flow chemistry method provides even greater advantages.

The individual synthesis step of the method according to the invention will now be described in more detail with reference to the following non-limiting experimental examples and analytical data.

Synthesis Step 1: Preparation of tert-butyl-4-chloro phenyl carbamate

Scheme 1: Batch synthesis preparation of compound 26

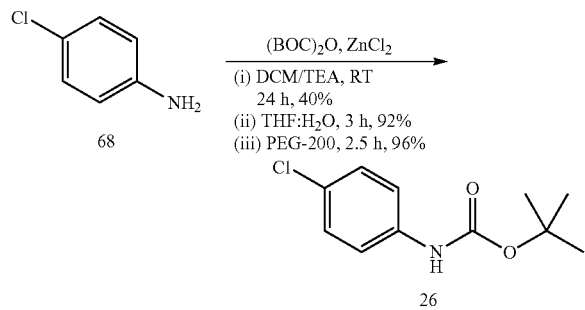

Scheme 1 shows the first synthesis step of the method in which 4-chloroaniline 68 was reacted with di-tert-butyl dicarbamate in a batch process to protect compound 68 through the di-tert-butyl carbamate (BOC) group. The di-tert-butyl dicarbamate reaction was chosen as the protecting group for 4-chloroaniline 68 from a host of possible protection reactions because of its ease of instalment and removal, its stability under metalation conditions, and the ease at which it can be cleaved under mild anhydrous acidic conditions. However, it is envisaged that many other similar protecting groups know from the literature could be employed in the first step of the method.

The tert-butyl-4-chlorophenylcarbamate of formula 26 was prepared from 4-chloroaniline 68 as shown in Scheme 1. The batch reaction was optimized by using three different reaction conditions and solvents.

In one experiment dichloromethane ("DCM") was used as solvent together with triethylamine as mild base. The reaction with triethylamine in DCM proceeded for about 24 hours. After reaction completion the reaction mixture was poured into ice cold water, with tert-butyl 4-chlorophenyl-carbamate 26 precipitating as white coloured solid (yield ca. 40%). Although the isolation process is simple the yield could be improved.

In another experiment the reaction was performed in a mixture of tetrahydrofuran ("THF") and water in a ratio of 1:1. The reaction in THF:water was completed in about 3 hours at a considerably better yield of ca. 92%. The compound again precipitated as white coloured solid from water as described above.

In another experiment a solvent free reaction consisting of 4-chloroaniline 68 and Boc anhydride was performed in the presence of PEG-200 (1 mL/g). It was noted that this reaction proceeded rapidly with a higher conversion rate compared to the reactions in DCM and THF. PEG-200 was recovered by evaporating the aqueous layer after completion of the reaction, and was used in a second reaction where the product yield (ca. 96%) was maintained. The product was collected by filtration as a white coloured solid and characterized by $^1$H-NMR, $^{13}$C-NMR, IR and elemental analysis.

Scheme 2: Flow synthesis preparation of compound 26

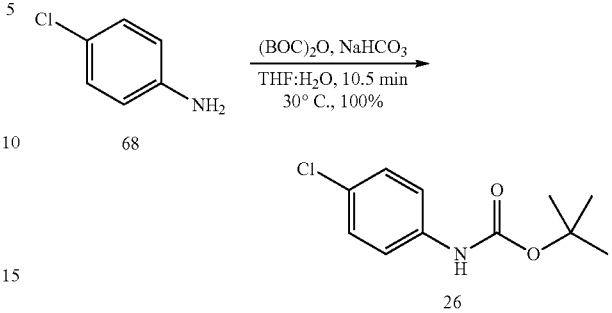

Figure 4:
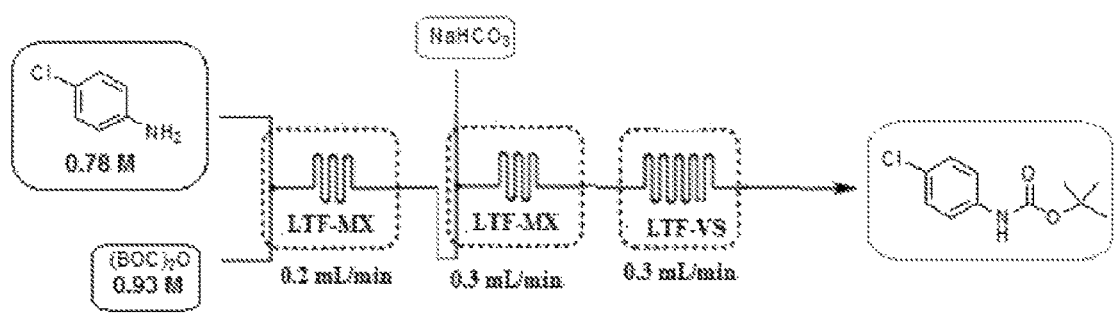
FIG. 4 shows a schematic representation of the experimental setup for step 1 of the flow synthesis reaction.

Preparation of tert-butyl-4-chloro phenyl carbamate 26 (Scheme 2) in flow was done by using Chemyx Fusion syringe pumps and LTF microreactors. The flow reaction comprised reacting 4-chloroaniline 68 with di-tert-butyl dicarbamate in the presence of aqueous sodium bicarbonate as a base. The flow reaction was carried out as shown in FIG. 4, with concentrations of compound 68 and Boc anhydride at 0.78 M and 0.93 M respectively. The reaction conditions, including the THF:water solvent mixture, were selected to compare the results of the flow reaction with the batch reaction.

The effect of residence time, concentration of di-tert-butyl dicarbamate, and temperature on the conversion of compound 68 was investigated.

Figure 5:
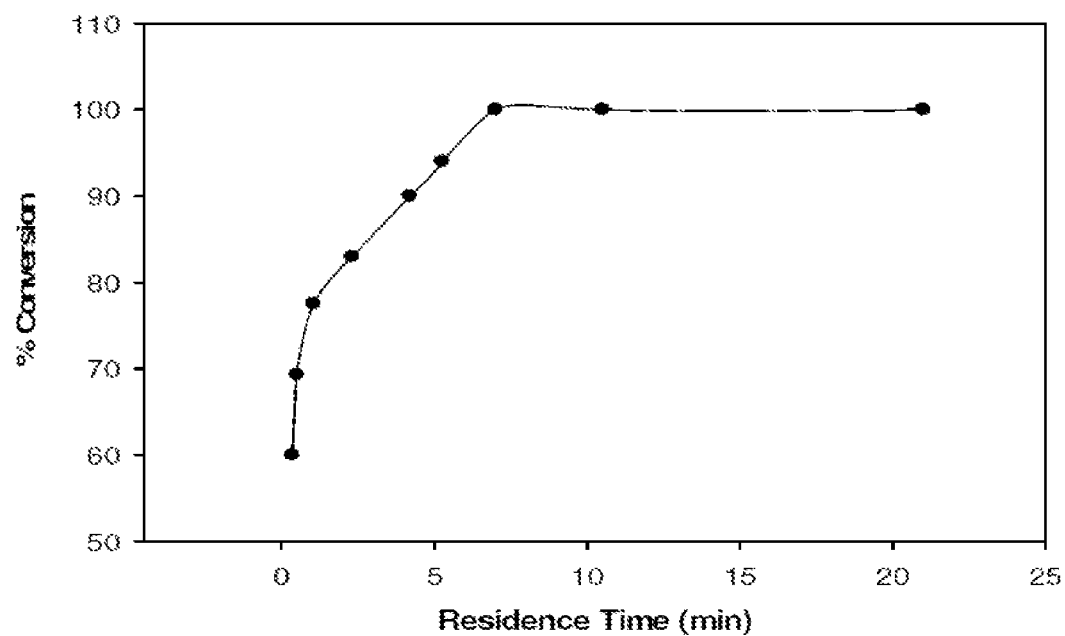
FIG. 5 shows a graphical representation of the effect of residence time on conversion of compound 68.

The flow reaction was first investigated for the effect of residence time by keeping the concentration of compound 68 at 0.78 M and the Boc anhydride at 0.93 M (1.2 equiv) while the reaction was carried out at the room temperature. Residence times of between 0.35 minutes and 21 minutes were investigated. Unsurprisingly, it was found that as the residence time decreases, the conversion of compound 68 decreased. It is well know that residence time is directly proportional to the volume of reactor and inversely proportional to the total flow rate. From FIG. 5 it can be seen that the maximum conversion for this experiment was observed at a residence time of about 7 minutes.

Figure 6:
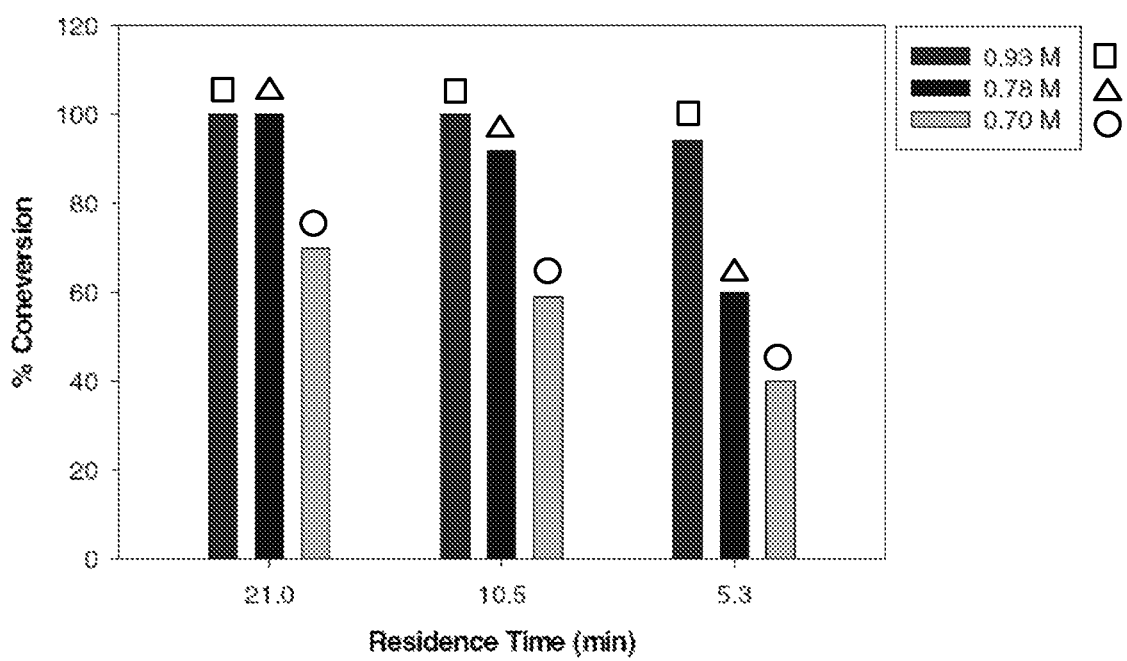
FIG. 6 shows a graphical representation of the effect of concentration of di-tert-butyl dicarbamate on conversion of compound 68.

The investigation into the effect of the concentration of di-tert-butyl dicarbamate on the conversion of compound 68 (0.78 M) was conducted by varying the molar concentration of di-tert-butyl dicarbamate from 0.93 M to 0.70 M at different residence times. The reactions were performed at room temperature at residence times of 5.25, 10.5 and 21.5 minutes, and di-tert-butyl dicarbamate concentrations of 0.70 M, 0.78 M, 0.93 M. The conversion of 4-chloroaniline 68 decreased with the decreased availability of the reagent, which led to an insufficient ratio of the reactants in a microreactor. The results of these experiments are shown in FIG. 6. It is seen that the maximum conversion is attained at 0.78 M di-tert-butyl dicarbamate.

Figure 7:
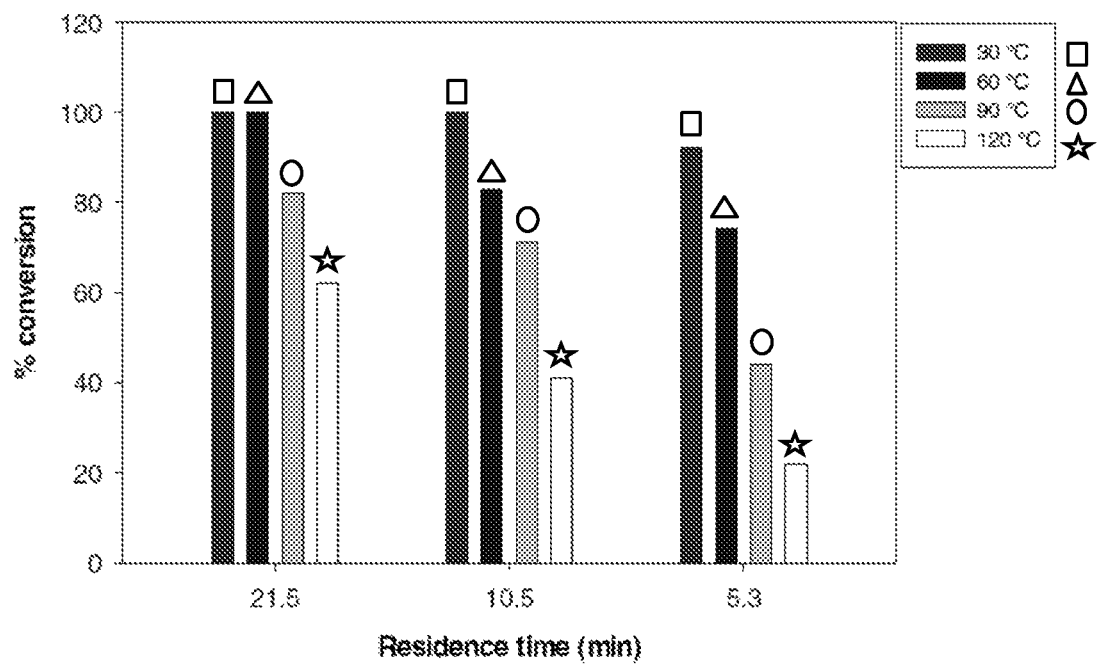
FIG. 7 shows a graphical representation of the effect of temperature on the conversion of compound 68.

The effect of temperature was investigated at residence times of 5.3, 10.5, and 21.5 minutes by varying the temperatures between 30° C. and 120° C. As the temperature increased the conversion of 4-chloroaniline 68 decreased. The findings of the temperature experiments are shown in FIG. 7.

From the above experiments it appears that the optimum conditions in a flow synthesis setup for the conversion of compound 68 is a residence time of about 10.5 minutes, temperature about 30° C., and a concentration ratio for compound 68 to Boc anhydride of about 1:1 to about 1:2.

Synthesis Step 2: Preparation of tert-butyl-4-chloro-2-(2,2,2-trifluoroacetyl) phenyl carbamate Scheme 3: Batch synthesis preparation of compound 27

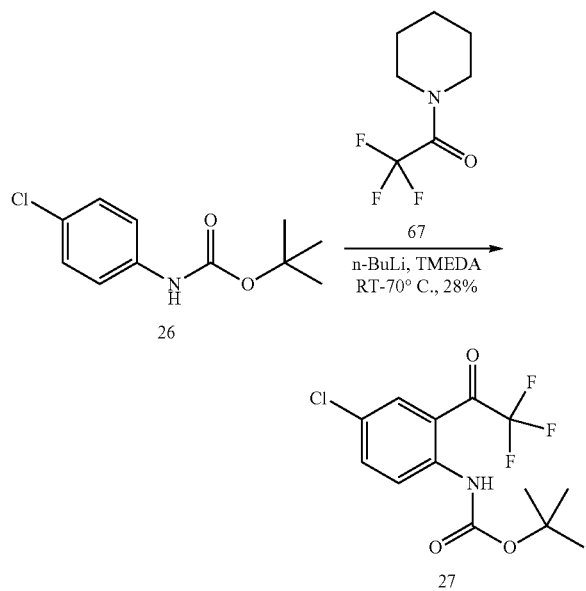

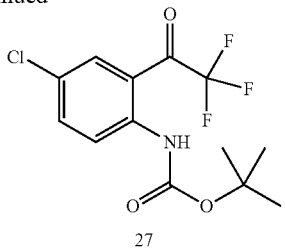

Scheme 3 shows the reaction step for the conversion of tert-butyl 4-chlorophenylcarbamate 26 to tert-butyl-4-chloro-2-(2,2,2-trifluoroacetyl) phenyl carbamate 27.

Ortho lithiation of compound 26 has only previously been reported to occur with tert-butyllithium and sec-butyllithium. It was found that compound 26 could also be lithiated with excess n-butyllithium, which is safer and more suitable for use on large scale. After addition of n-butyllithium to compound 26 in THF, the reaction mixture turned from white to a yellow-orange suspension, the metalation was continued at −70° C. to room temperature for 1 hour, subsequently the liberated dianion was quenched at −55° C. with piperidine trifluoroacetic acid 67 as the trifluoro acetylating agent to afford tert-butyl 4-chloro-2-(2,2,2-trifluoroacetyl) phenylcarbamate 27. It should be noted that the reaction could also be performed with another trifluoro acetylating agent such as ethyl trifluoro acetate. The reaction yielded a light yellow coloured solid (yield ca. 28%).

Scheme 4: Flow synthesis preparation of compound 27

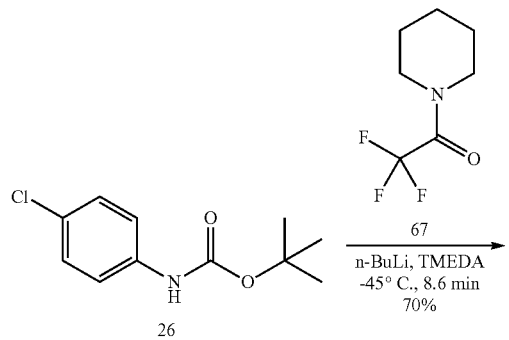

Figure 8:
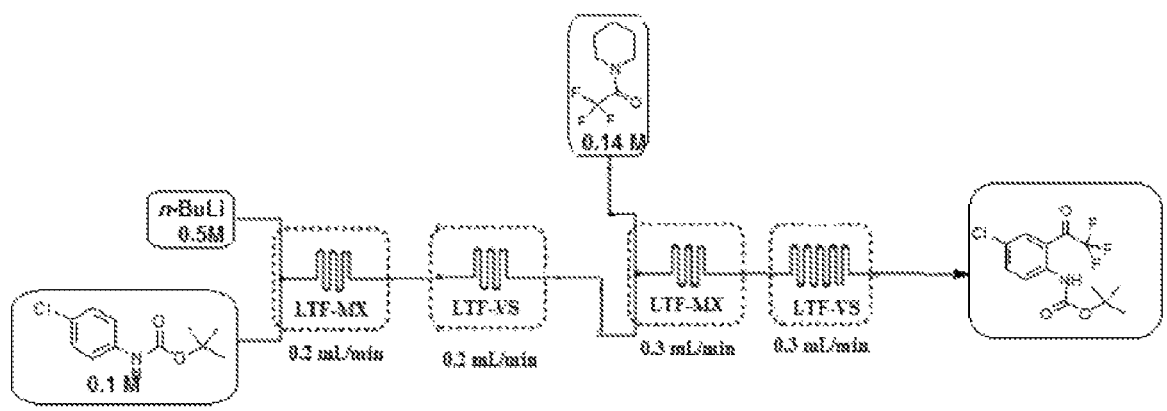
FIG. 8 shows a schematic representation of the experimental setup for step 2 of the flow synthesis reaction.

A flow reaction according to Scheme 4 was performed with the experimental setup as shown in FIG. 8. The concentrations of the reagents were selected based on the corresponding batch experiments for ease of comparison. After preliminary confirmation of the reaction in the microreactor, reaction conditions were investigated for the effect of temperature, residence time and concentration on conversion of compound 26.

The conversion of compound 26 to compound 27 in flow was first investigated for the effect of temperature. The temperature of the reaction was varied from −70° C. to 0° C. The reaction was carried out at a concentration of 0.5 M of n-butyllithium, 0.1 M of compound 26, 0.14 M of compound 67, with a flow rate of 0.3 mL/min. The concentrations were selected based on batch results experiments.

Figure 9:
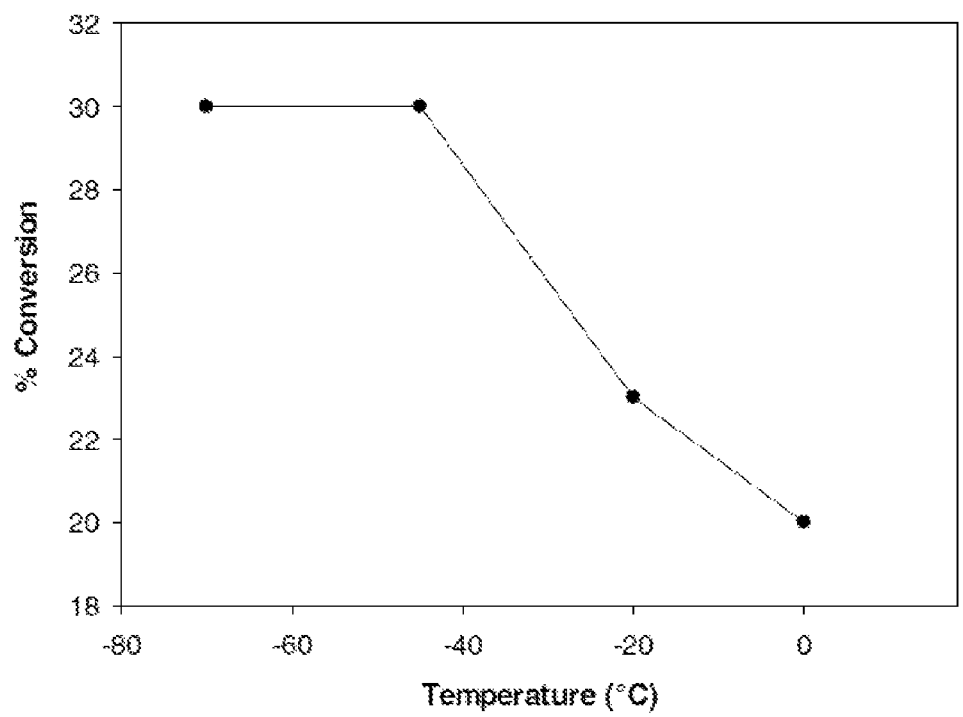
FIG. 9 shows a graphical representation of the effect of temperature on the conversion of compound 26 in flow.

It was noted that an increase in temperature results in a decrease in the conversation of compound 26, most likely because of decomposition of n-butyllithium at higher temperatures in THF. From FIG. 9 it can be seen that a maximum conversion was observed in the range of about −70° C. to about −40° C. In the semi continuous flow method the reaction proceeded at a higher temperature and comparatively more conversion (70%) was compared to the batch setup (−78° C., 28% conversion).

Figure 10:
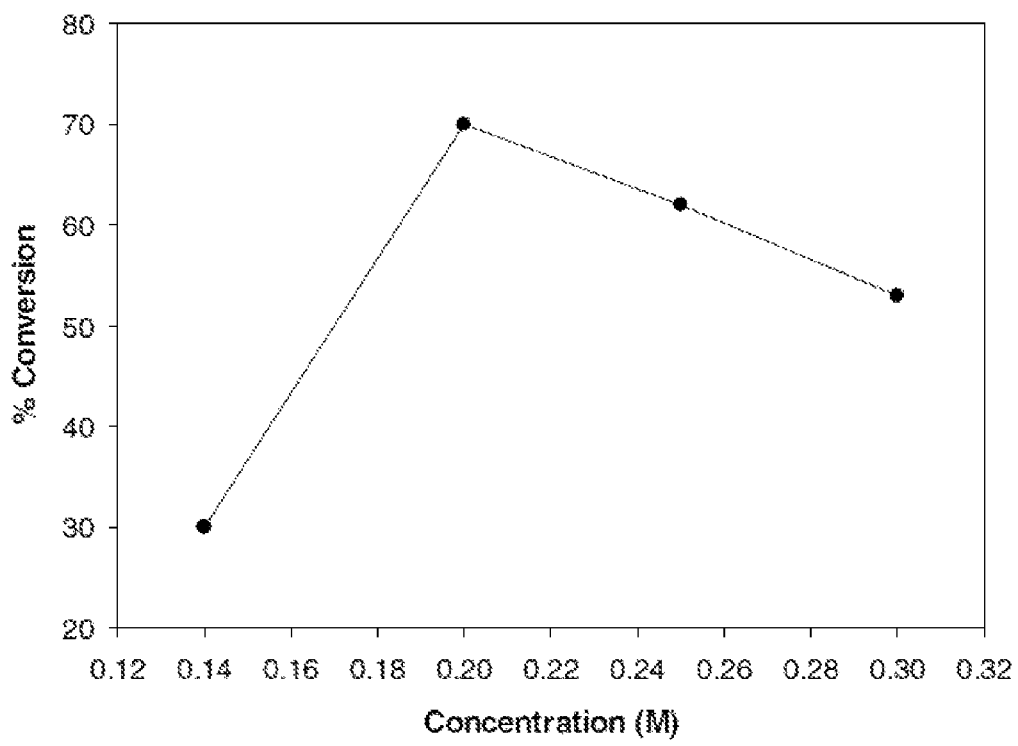
FIG. 10 shows a graphical representation of the effect of the concentration of compound 67 on the conversion of compound 26 in flow.

The effect of the concentration of the trifluoro acetylating agent, compound 67, was investigated. The concentrations of the other two reagents were kept constant at 0.25 M n-butyllithium and 0.1 M of compound 26, flow rate 0.3 mL/min (residence time 8.6 minutes, temperature at −45° C.). From FIG. 10 it can be seen that the conversion of compound 26 increased with an increase in the concentration of compound 67 up to a certain point. From this analysis it appears that, for this set of parameters, an optimum concentration was found in the range of 0.18 to 0.22 M, i.e. about 2 molar equivalents.

Figure 11:
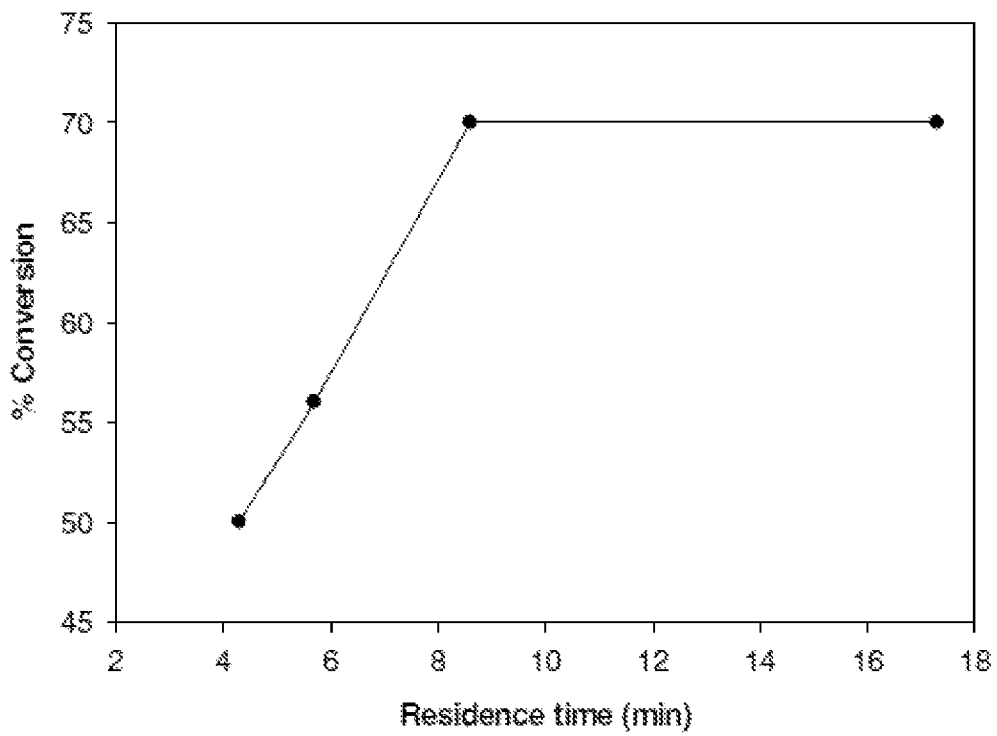
FIG. 11 shows a graphical representation of the effect of residence time on conversion of 27 in flow.
Figure 12:
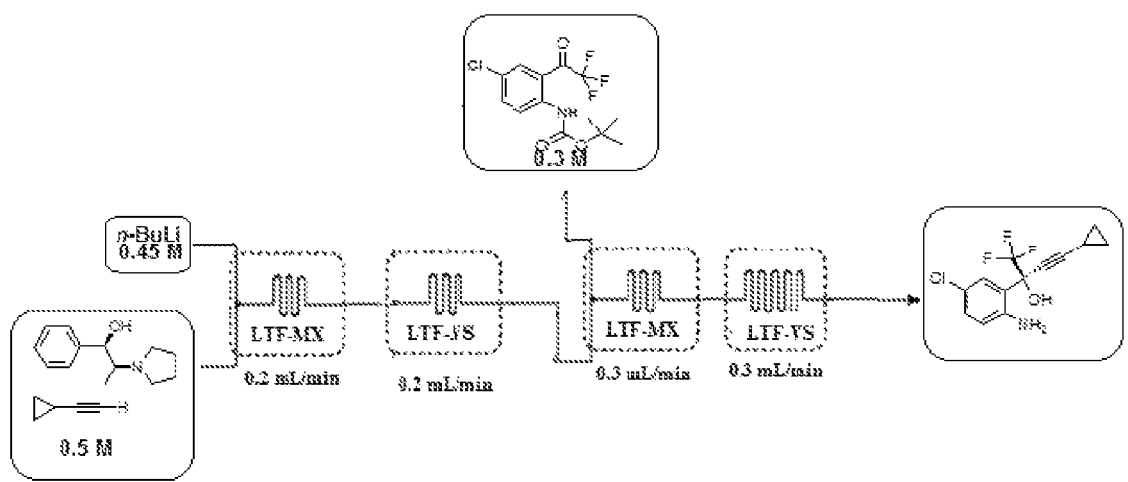
FIG. 12 shows a schematic representation of the experimental setup for step 3 of the flow synthesis reaction.

After the investigation into optimized concentration conditions (0.25 M n-butyllithium, 0.1 M compound 26, 0.2 M compound 67) and temperature (−45° C.), the effect of residence time on the conversion of compound 26 was investigated. The above mentioned concentrations and temperature were kept constant throughout these experiments. The effect of residence time on the conversion of 26 is shown in FIG. 11. The experiments started at a residence time of 17.3 minutes, which achieved a 70% conversion. As can be seen from FIG. 11, at these conditions the residence time can be reduced to about 8 minutes without a loss in conversion.

Overall the flow reaction in step 2 compares very favourably with what was observed in batch. A summation is provided in table 1 below.

TABLE 1

A comparison of reaction conditions and conversion for step 2 in batch vs. flow.

| | Reaction time (min) | Concentration (M) | | | Temperature (° C.) | Conv |
| --- | --- | --- | --- | --- | --- | --- |
| | | n-BuLi | Pip. Trifluoroacetic acid | compound 26 | | |
| Batch | 180 | 0.5 | 0.14 | 0.1 | −70 | 28 |
| Microreactor | 7.7 | 0.25 | 0.2 | 0.1 | −45 | 70 |

Synthesis Step 3: Preparation of (S)-2-(2-amino-5-chlorophenyl)-4-cyclopropyl-1,1,1-trifluoro-3-butyn-2-ol Scheme 5: Batch synthesis preparation of compound 56

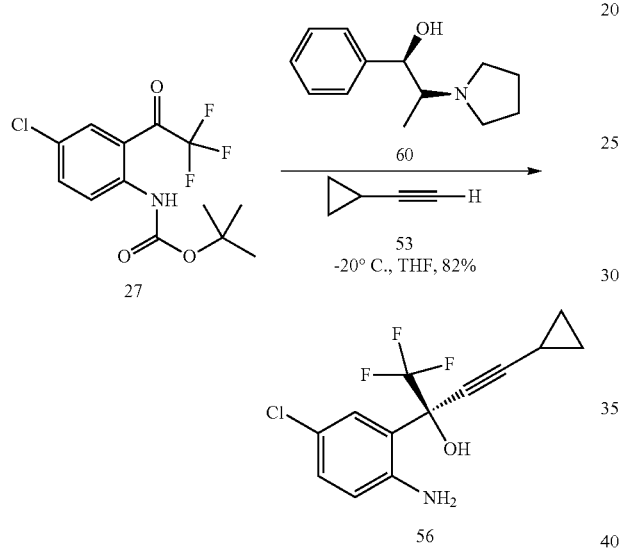

Step 3 in the method according to the present invention generates the chiral centre of the final product. Scheme 5 shows the batch reaction for the preparation of (S)-2-(2-amino-5-chlorophenyl)-4-cyclopropyl-1,1,1-trifluoro-3-butyn-2-ol 56 through the addition of cyclopropyl acetylene 53 and (1R,2S) N-pyrrolidinylnorephedrine 60 to the tert-butyl 4-chloro-2-(2,2,2-trifluoroacetyl) phenylcarbamate 27 prepared in step 2. The mixture (compounds 60 and 53) was cooled to −20° C. and to this solution n-butyllithium and compound 27 was added dropwise under nitrogen. The resulting orange coloured solution was stirred for 1 hour at that temperature, then the reaction was quenched by the addition of 6N HCl. The mixture was warmed to ambient temperature, extracted with ethyl acetate and evaporated to get the product as fine yellow powder of compound 56 in 82% yield after purification by using flash column chromatography (10% ethyl acetate and hexane). (1R,2S) N-Pyrrolidinylnorephedrine 60 was used in this reaction as a chiral additive, which promotes enantioselective alkylation.

After completion of the reaction, the product was analyzed for chiral purity using Cyclobond I 2000 chiral column, methanol and water (80:20) as mobile phase. In this the product peak as major (97.8% at 2.42 min) and other isomer (2.2% at 3.5 min) and it was compared with standard (99% purity at 2.42 min).

The product was purified by recrystallization with 10:1 heptane:toluene at 25° C. for 3 h to afford the pure compound. After purification the compound 56 was again tested for chiral purity, which had now increased to 98.9%.

In another embodiment of the invention, steps 2 and 3 as described above may be replaced by preparing (S)-2-(2-amino-5-chlorophenyl)-4-cyclopropyl-1,1,1-trifluoro-3-butyn-2-ol 56 from compound 26 by using cyclopropylethynyl trifluoromethyl ketone 29 according to the reaction shown in Scheme 6 below.

Scheme 6: Alternative catch synthesis preparation of compound 56 from compound 26.

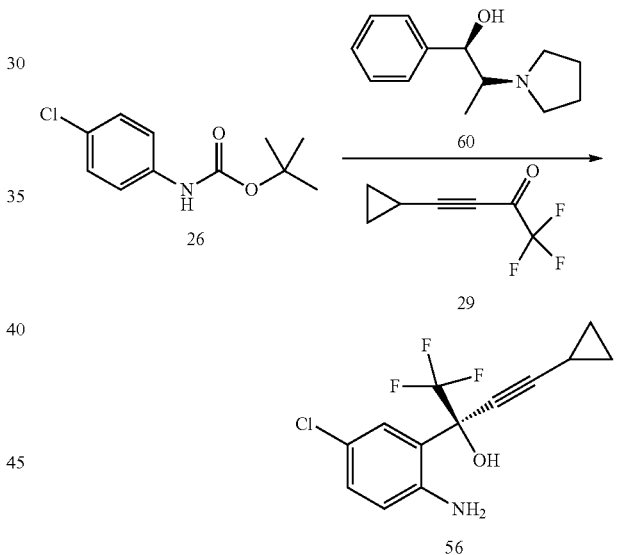

The 4-chlorophenylcarbamate 26 was cooled to −55° C. and 5 equivalents of n-butyllithium was added. The liberated dianion was quenched with cyclopropylethynyl trifluoromethyl ketone 29 to afford compound 56 in 47% yield after purification by flash column chromatography eluting with 10% ethyl acetate and hexane. The chiral purity of the compound was tested by using HPLC. The chiral column (Cyclobond I 2000) used as stationary phase and methanol:water (80:20) used as mobile phase. The results obtained from the chromatogram were matched with the standard compound. The major peak was observed at 2.49 min with 86.5% purity.

The flow experiments were performed according to Scheme 7 below in which compound 27 was converted to compound 56 in the presence of the chiral axillary 60 by the addition of compound 53.

Scheme 7: Flow synthesis preparation of compound 56

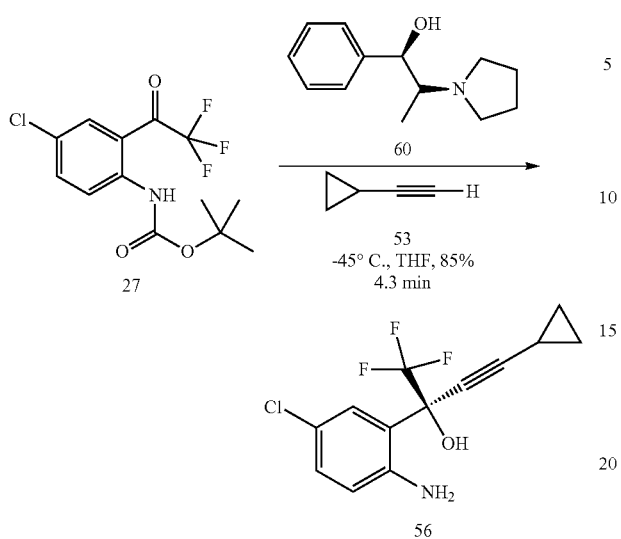

The initial flow reaction experiments were based on the batch reaction parameters after which the reaction was optimized by investigation of the effect of residence time, concentration and temperature.

Figure 13:
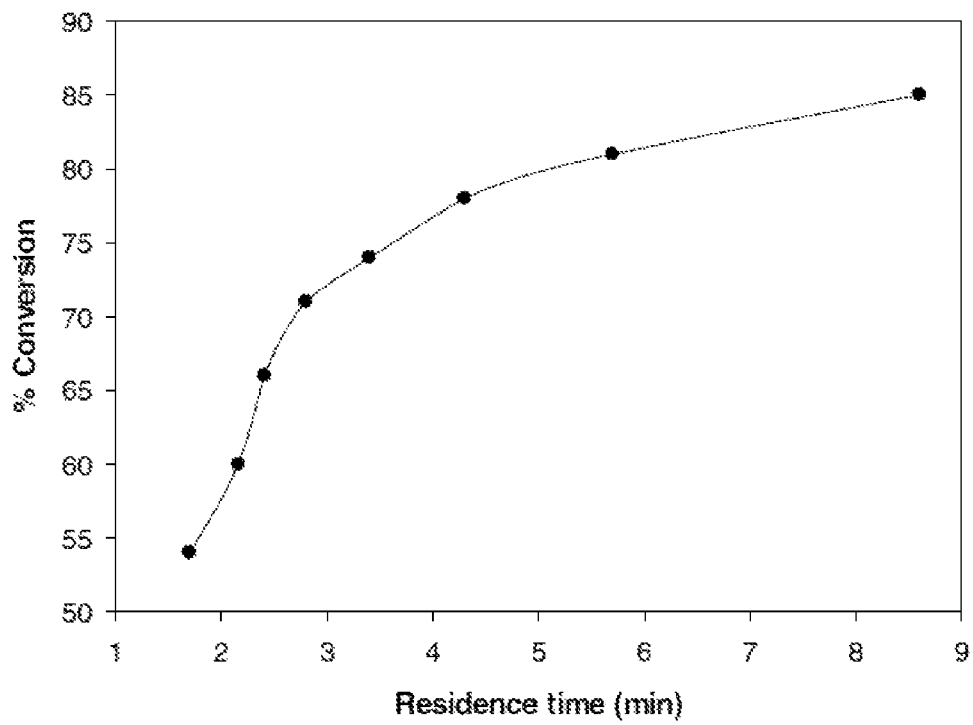
FIG. 13 shows a graphical representation of the effect of residence time on the conversion of compound 27 in flow.

Initial residence time experiments were performed at the 0.45 M n-butyllithium, 0.5 M compound 53, and 0.35 M compound 27 in THF. The reaction temperature was maintained at −45° C. The investigation into residence time was conducted in the range of about 8.6 minutes to about 1.7 minutes. FIG. 13 shows that an optimum conversion was attained at 8.6 minutes.

Figure 14:
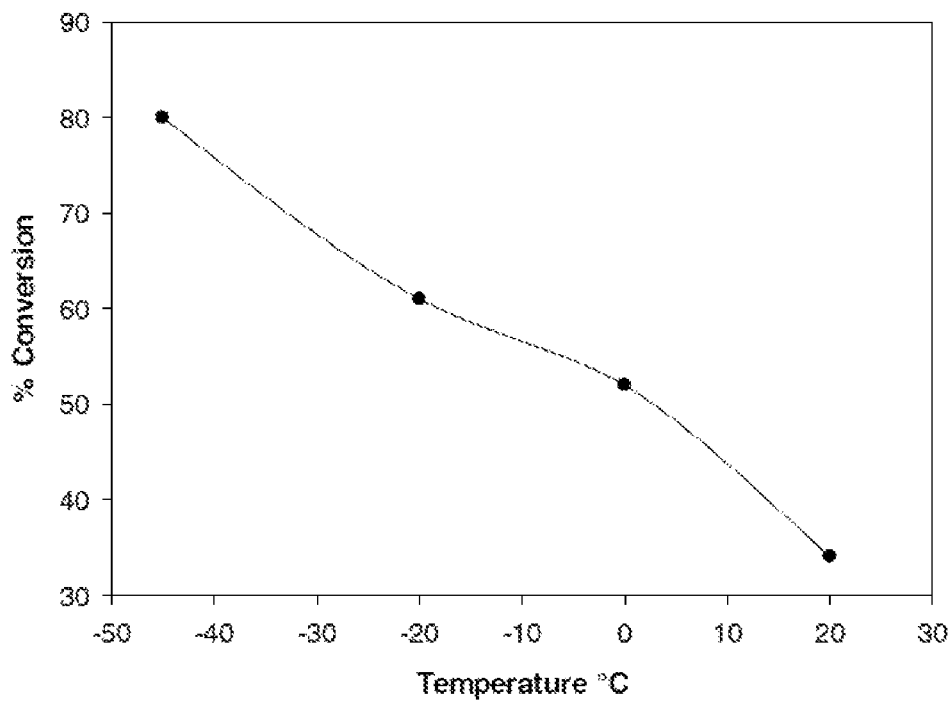
FIG. 14 shows a graphical representation of the effect of temperature on conversion of 27 in flow.

The effect of temperature on the conversion of compound 27 was investigated at 0.45 M n-butyllithium, 0.5 M compound 53, and 0.35 M compound 27 with a residence time was 4.3 minutes. The effect of temperature on the conversion of compound 27 is represented in FIG. 14.

Figure 15:
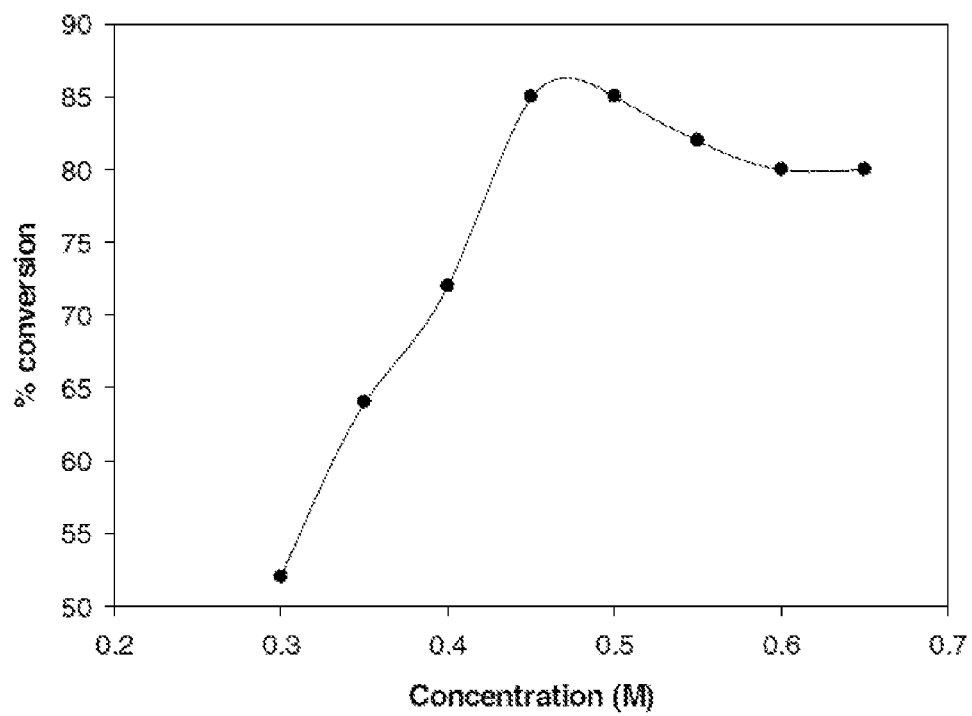
FIG. 15 shows a graphical representation of the effect of concentration of compound 53 on the conversion of compound 56 in flow.
Figure 16:
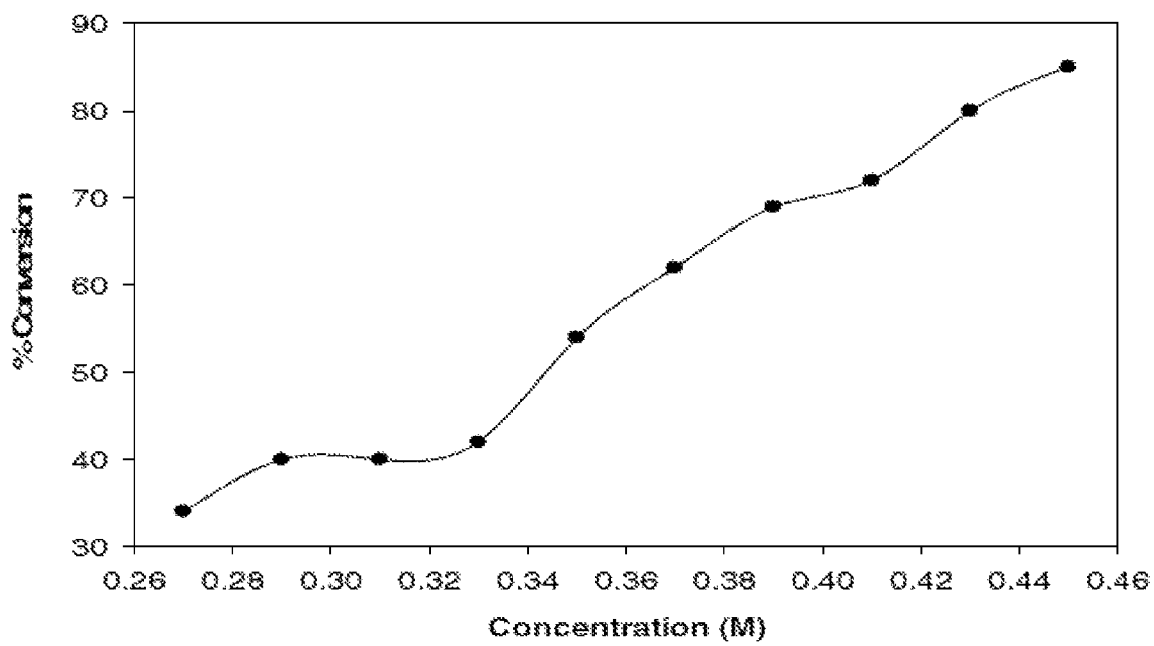
FIG. 16 shows a graphical representation of the effect of concentration of n-butyllithium on the conversion of compound 56 in flow.

In further experiments the effect of the concentrations of cyclopropyl acetylene 53 and n-butyllithium on the conversion of compound 27 were investigated. Previously, at a concentration of 0.45 M of compound 53 a 85% conversion was obtained at a residence time of 4.8 minutes. Investigations were conducted at 0.45 M n-butyllithium and 0.35 M of compound 27, at a temperature of −45° C. The effect of the concentration of cyclopropyl acetylene 53 on conversion is shown in FIG. 15. Experiments into the effect of the concentration of n-butyllithium were conducted between 0.45 M and 0.27 M. The concentration of cyclopropyl acetylene 53 was 0.45 M, that of compound 27 was 0.35 M, and the temperature was kept at −45° C. The effect of the concentration of n-butyllithium on conversion is shown in FIG. 16.

Synthesis Step 4: (S)-6-chloro-(cyclopropylethynyl)-1,4-dihydro-4-(trifluoromethyl)-2H-3,1-benzoxazin-2-one Scheme 8: Batch synthesis preparation of efavirenz (compound 8)

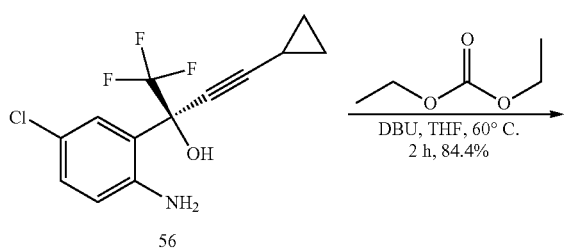

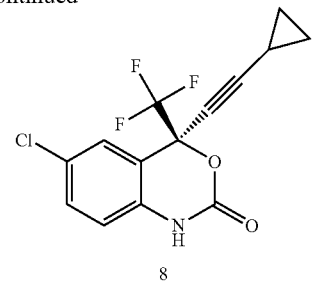

Scheme 8 above shows the batch reaction for the final step of the method. The optically pure (S)-2-(2-amino-5-chlorophenyl)-4-cyclopropyl-1,1,1-trifluoro-3-butyn-2-ol (amino alcohol) 56 was reacted with carbonyl delivering agent (di ethyl carbonate) in the presence of 1,8-diazabicyclo[5.4.0]undec-7-ene (DBU) at 60° C. in a cyclisation reaction to give optically pure (S)-6-chloro-(cyclopropylethynyl)-1,4-dihydro-4-(trifluoromethyl)-2H-3,1-benzoxazin-2-one 8 (efavirenz). After recrystallization with 5% ethyl acetate in heptane the compound was tested for the chiral purity by using HPLC with Cyclobond I 2000 column. The chromatogram showed 99% purity at 2.51 min and it was matched with the standard compound chromatogram (2.51 min, 99% purity).

Figure 17:
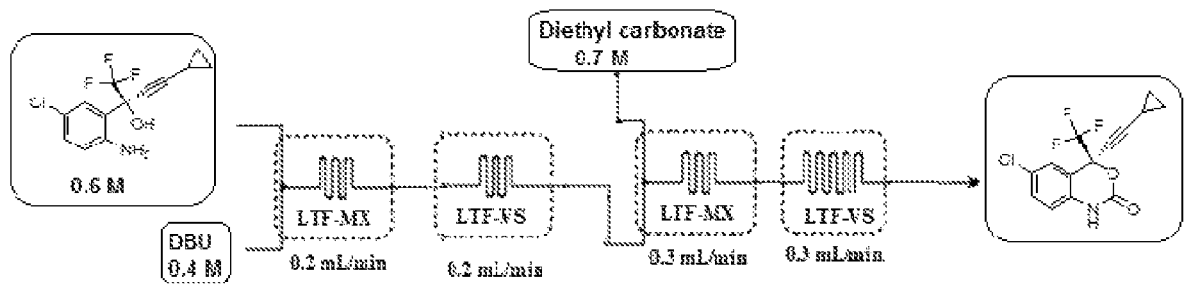
FIG. 17 shows a schematic representation of the experimental setup for step 4 of the flow synthesis reaction.

The cyclisation reaction in flow was performed according the reaction Scheme 9 below, and with the experimental setup depicted in FIG. 17.

Scheme 9: Flow synthesis preparation of efavirenz (compound 8)

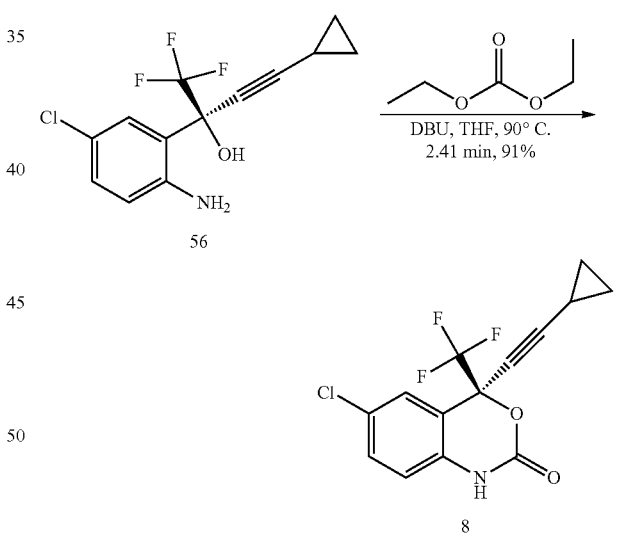

Figure 18:
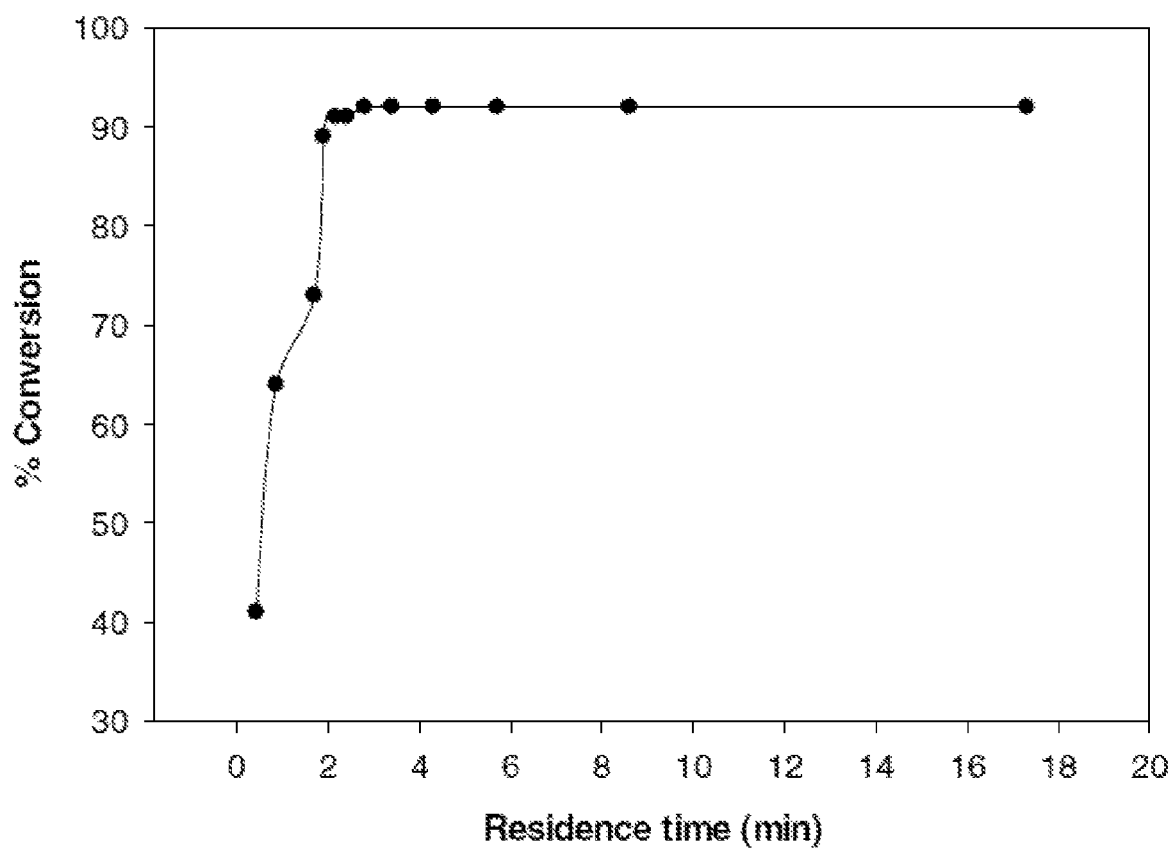
FIG. 18 shows a graphical representation of the effect of residence time on the conversion of compound 56 in flow.
Figure 19:
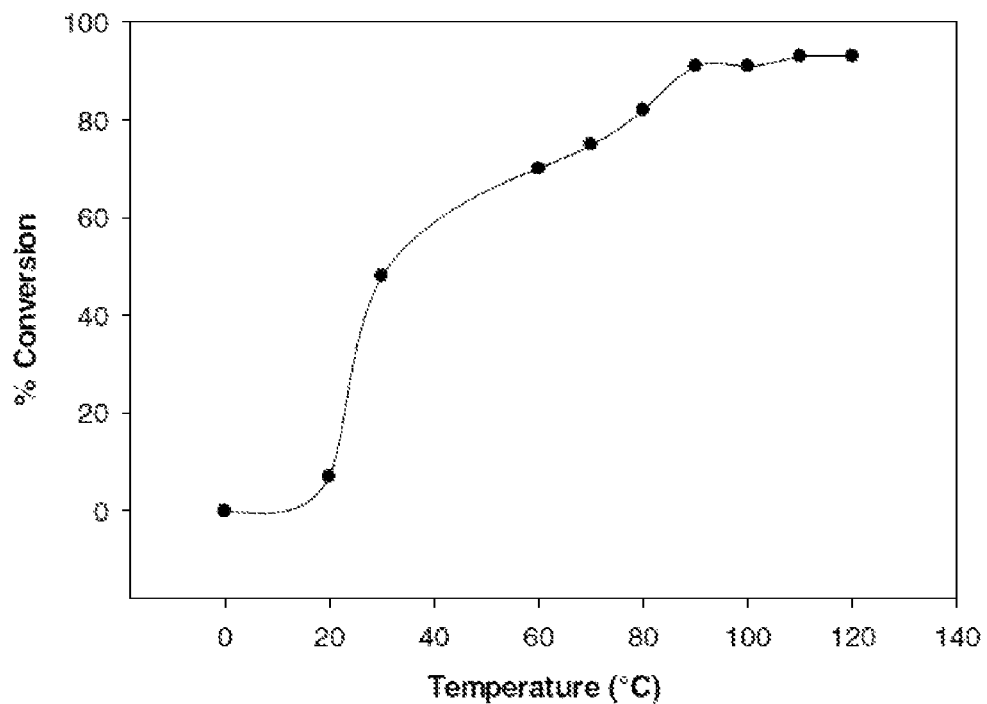
FIG. 19 shows a graphical representation of the effect of temperature on the conversion of compound 56 in flow.

As with the prior steps of the flow method, the effect of different residence times, temperatures, and concentrations on the conversion of compound 56, were investigated. For the residence time experiments reagent concentrations of 0.60 M of compound 56, 0.40 M of DBU, and 0.70 M of diethyl carbonate (DEC) were used at a temperature of 90° C. The effect of residence time on the conversion of compound 56 is shown in FIG. 18. As can be seen from FIG. 18, unexpectedly, excellent conversion was still obtained a residence time of 2.8 minutes.

The effect of temperature was investigated around 90° C., as used in the batch process. Concentrations of 0.60 M of compound 56, 0.40 M of DBU, and 0.70 M of DEC were used with a residence time of 2.41 min. The investigation into the effect of temperature was conducted in a range of 0° C. to 120° C., with the increasing from 0% to about 93%.

Figure 20:
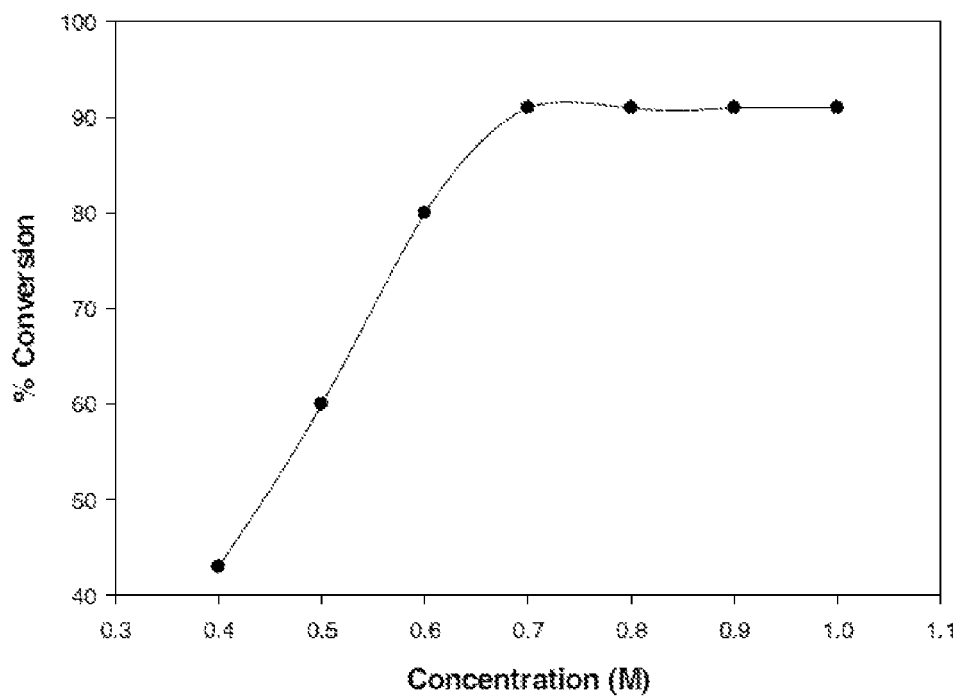
FIG. 20 shows a graphical representation of the effect of the concentration of diethyl carbonate on the conversion of compound 56 in flow.

Finally, the effect of the concentration of diethyl carbonate on the conversion of compound 56 was investigated. For these experiments the concentrations of the other reagents were 0.60 M of compound 56 and 0.40 M of DBU with the temperature kept at 90° C. The effect of the concentration of diethyl carbonate on the conversion of compound 56 is shown in FIG. 20.

As can be seen from the reaction schematic in FIG. 3, a semi continuous flow method for the synthesis of optically pure efavirenz was developed with excellent yields at each step of the method.

Experimental Parameters and Analytical Data for Batch Reactions

All the reagents (analytical grade) were purchased from Sigma Aldrich and were used without purification. Air and moisture sensitive reactions were carried out under an atmosphere of nitrogen in oven-dried glassware (reagent flasks) that was allowed to cool to room temperature under high vacuum. Tetrahydrofuran (THF) was dried according to known methods and stored over activated 4 Å° molecular sieves and subjected to Karl-Fisher analysis. All the solvents used were anhydrous and the solvents removed by rotary evaporator. Brine solution refers to saturated sodium chloride solution. (1R,2S)—N-Pyrrolidinylnorephedrine, cyclopropyl acetylene and piperidine trifluoroacetic acid, were prepared as shown in the literature. Reactions were monitored by thin-layer chromatography (TLC) and gas chromatography (GC).

TLC carried out on 0.25 mm E. Merck silica gel plates (60F-254) using UV light as a visualizing agent, and either ninhydrin, cerium sulfate, cerium ammonium molybdate or potassium permanganate staining solutions and heat as developing agents.

GC was carried out on Agilent 7820A instrument using a $DB_5$ column equipped with a flame ionization detector and ultra-high purity nitrogen carrier gas at a flow rate of 2.8 mL/min. Oven temperature was maintained at 100° C. for 3 min and then ramped to 324° C. (hold time 5 min) at 35° C./min with a total run time of 16.4 min. Chiral HPLC was carried out using an Agilent 1220 Infinity LC instrument using Cyclobond I 2000 column equipped with diode array detector, flow rate 1 mL/min, mobile phase:methanol/DI water; 80:20, DAD, which gave optimum detection at 252 nm with a total runtime of 30 min.

Nuclear magnetic resonance (NMR) spectra were recorded using Bruker spectrometer (Bruker Ultrashield™ 400 plus) which was operated at 400 MHz for proton and 100 MHz for carbon. Spectra were calibrated using the residual $^1H$ chemical shift in $CDCl_3$ (7.26 ppm) or DMSO $d_6$ (2.62 ppm) which was used as the internal reference standards for $^1H$ NMR and $^{13}C$ NMR Spectroscopy. The chemical shift values for all spectra are given in parts per million (ppm). The following abbreviations were used to explain NMR data, s=singlet, d=doublet, t=triplet, q=quartet, m=multiplet.

The FTIR characteristic peaks were recorded on a Bruker Platinum Tensor 27 spectrophotometer with an ATR fitting. The analyses of samples were recorded in the range 4000-400 $cm^{-1}$ and the peaks are reported in wavenumbers ($cm^{-1}$). The solid and liquid samples were analyzed without any modification.

Elemental analysis was performed using a CHNS analyzer and the data reported in percentages.

1. Preparation of 4-cyclopropylactylide (Compound 53)

A three-necked round-bottomed flask was equipped with a pressure-equalizing addition funnel and a reflux condenser that is fitted with a nitrogen inlet. The flask was charged with 5-chloro-1-pentyne (5 g, 49.01 mmol) and cyclohexane (50 mL), and the mixture cooled to −20° C. To this reaction mixture, n-butyllithium (49 mL, 2.5 M in cyclohexane, 122.5 mmol) was added dropwise via the addition funnel over 1 hour maintaining the temperature at −20° C. After the addition was completed the reaction mixture turned into a thick precipitate at this time the reaction mixture was heated to reflux (78° C.) and maintained at reflux for 3 hours. The completion of the reaction was monitored by TLC (20% ethyl acetate in hexane) and GC. After completion, the reaction was cooled to 0° C. to −10 OC and then quenched carefully by the dropwise addition of aqueous saturated ammonium chloride (35 mL). The aqueous layer was separated and the organic layer is fractionally distilled. The boiling range of 35-78° C. was collected. Which consists of 60-80% of cyclopropyl acetylene 53 (1.4 g, 50%); this fraction was distilled a second time and the boiling range of 52-55° C. collected. After the distillation, the obtained pure product was analyzed by NMR and IR spectroscopy, the resulting spectra correlating with reported standard compound spectra.

$^1H$-NMR-(400 MHz) in $CDCl_3$: δ 0.69-0.80 (m, 4H); 1.21-1.27 (m, 1H); 1.76 (s, 1H). $^{13}C$-NMR in $CDCl_3$ (100 MHz): 2.1.4.0, 11.0, 70.2, 87.4. IR ($cm^{-1}$) 1157, 2120, 2873, 3302, 3374.

2. Preparation of 4-cyclopropyl-1,1,1-trifluoro-but-3-yn-2-one (Compound 29)

n-Butyllithium (49 mL, 2.5 M in cyclohexane) was slowly added via an addition funnel to 250 mL two-neck round-bottomed flask which was charged with 5-chloro-1-pentyne (5 g, 49.01 mmol) in THF (50 mL) at −28° C., then the reaction mixture temperature was kept below 0° C. and stirred for 4 hours. After that the reaction mixture was cooled to −55° C. and piperidine trifluoroacetic acid (8.12 mL, 53.91 mmol) was added slowly. After 1 hour at same temperature, the reaction mixture was quenched with 2N HCl and the organic and aqueous layers were separated. After evaporation of the organic layer using a rotary evaporator the residue was washed with water (100 mL) and brine solution (100 mL) and extracted with ethyl acetate (3×100 mL). The combined organic layers were dried over anhydrous $Na_2SO_4$ and the crude product was distilled in vacuo. After distillation, the product was obtained as a pale yellow oil 29 (2.76 g, 40%). This resulting compound was further subjected to analytical techniques (NMR and IR) that matched with the reported product.

$^1H$-NMR-(400 MHz) in $CDCl_3$: δ 1.20-1.25 (m, 4H); 1.55 (m, 1H). $^{13}C$-NMR in $CDCl_3$ (100 MHz): 11.1, 68.2, 72.5, 114.3, 166.3. IR ($cm^{-1}$) 2209, 1705, 1217, 1163, 1066, 920.

3. Preparation of N-Piperidine Trifluoro Acetic Acid (Compound 67)

Piperidine (5.8 mL, 58.8 mmol) was added to a 250 mL two neck round-bottomed flask which is previously charged with a mixture of dichloromethane (45 mL) and triethylamine (12.2 mL, 88.2 mmol). To this mixture trifluoroacetic anhydride (11.5 mL, 81.8 mmol) was added, the resulting reaction mixture was stirred at room temperature for 3-4 hour and the completion of reaction was monitored by TLC (20% ethyl acetate in hexane) and GC. After completion of the reaction, the reaction mixture extracted with water, sodium bicarbonate and dil HCl. The organic layer separated and was dried in vacuo. The resulting pale yellow liquid was (8.5 g, 79.8%) subjected to NMR & IR spectroscopy.

$^1$H-NMR-(400 MHz) in CDCl$_3$: δ 1.57-1.63 (m, 6H); 3.47-3.54 (m, 4H). $^{13}$C-NMR in CDCl$_3$ (100 MHz): δ 4.5, 26.7, 28.0, 44.5, 130.9, 132.1.IR (cm$^{-1}$) 1184, 1286, 1465, 1682, 2863.

4. Preparation of (1R,2S)—N-pyrrolidinylnorephedrine (compound 60)

A round-bottomed flask equipped with a mechanical stirrer, condenser with Dean-Stark trap and with a nitrogen inlet, was charged with toluene (20 mL), (1R,2S) norephedrine (5 g, 33 mmol), 1,4-dibromobutane (4.2 mL, 36.2 mmol) and Na$_2$CO$_3$ (5.6 g, 68 mmol). The stirred heterogeneous reaction mixture was heated to reflux under a nitrogen atmosphere. Completion of reaction monitored by TLC and GC. After completion of the reaction the reaction mixture was cooled to ambient temperature, filtered through a sintered glass funnel to remove inorganic salts, and the cake was washed with toluene (3×10 mL). The combined filtrate washed with water (2×25 mL). The organic layer was separated and concentrated under reduced pressure. The toluene solution was cooled to 10-15° C. and hydrochloric acid (HCl) in 2-propanol (0.275 mol) was added slowly. During the acid addition, the product precipitates as its hydrochloride salt (5.4 g, 80%). The salt compound analyzed by 1H-NMR & 13C-NMR and IR for the structural conformation.

$^1$H-NMR-(400 MHz) in CDCl$_3$: δ 1.14-1.27 (m, 3H); 2.08-2.29 (m, 4H); 3.04 (s, 2H); 3.31 (d, J=6.24, 1H); 3.85 (d, J=2.28, 1H); 4.15 (d, J=4.56, 1H); 5.59 (d, J=9.36, 1H); 7.42-7.20 (m, 5H); 11.85 (d, J=2.28, 1H). $^{13}$C-NMR-(100 MHz) in CDCl$_3$: δ 14.5, 28.0, 56.3, 69.7, 72.7, 130.9, 132.1, 133.1. IR-(cm$^{-1}$) 960, 1199, 1356, 1467, 1602, 2838, 2985, 3177.

5. Preparation of tert-butyl-4-chloro phenyl carbamate (Compound 26)

Preparation of compound 26 was done by using three different methods, as presented below, to improve the reaction yield and reduce the reaction time.

a) Method A

Triethylamine (7 mL, 78.74 mmol) was added to a solution of 4-chloroaniline 68 (5 g, 39.3 mmol) in dichloromethane (50 mL), and to this ZnCl$_2$ (5.35 g, 39.37 mmol) was added and stirred for 30 min at room temperature. Subsequently di-tert-butyl dicarbamate (9.13 mL, 43.3 mmol) was added dropwise to the above reaction mixture and stirred for 24 hours. The completion of the reaction was monitored by TLC (20% ethyl acetate in hexane) and GC. After completion of the reaction, the reaction mixture was poured into ice cold water and the product was precipitated as a lumpy cream-colored solid. Which is further extracted with ethyl acetate (3×50 mL), the combined organic layers were washed with water (25 mL), brine solution (25 mL) and dried over anhydrous Na$_2$SO$_4$. The resulting organic layers evaporated by rotary to give product 26 as a white coloured solid (3.56 g, 40%). This compound was analyzed by NMR, IR spectroscopy and elemental analysis.

$^1$H-NMR (400 MHz) in CDCl$_3$: δ 1.22 (s, 9H); 7.33 (d, J=8.44, 2H); 7.69 (d, J=8.40, 2H); 9.31 (s, 1H). $^{13}$C-NMR in CDCl$_3$ (100 MHz): δ 27.6, 40.2, 81.0, 122.1, 127.1, 128.4, 138.8, 177.0. IR (cm$^{-1}$): 1172, 1368, 1475, 1652, 2872, 2910, 3290. Anal. calcd for C$_{11}$H$_{14}$ClNO$_2$: C, 58.03, H, 6.20, N, 6.15, Found: C, 58.08, H, 6.16, N, 6.11.

b) Method B

4-Chloroaniline 68 (5 g, 39.3 mmol) was added into a 100 mL round bottom flask charged with a 1:1 ratio of THF and water (50 ml) and stirred until the compound dissolved, to this di-tert-butyl dicarbamate (9.13 mL, 43.3 mmol) was added dropwise and stirred for 3 hours at room temperature. The completion of the reaction was monitored by TLC (20% ethyl acetate in hexane) and GC. After completion, the reaction mixture extracted with ethyl acetate (3×50 mL), washed with water (50 mL) and brine solution (50 mL). The resulting organic layer dried over anhydrous Na$_2$SO$_4$ and evaporated under reduced pressure to get product as white coloured solid (8.1 g, 92%) which was analytically compared with Method A results.

c) Method C

A mixture of 4-chloroaniline 68 (5 g, 39.3 mmol) and di-tert-butyl dicarbamate (9.13 mL, 43.3 mmol) in PEG-200 (5 mL, 7.8 mmol) was stirred at ambient temperature until TLC indicated the total disappearance of the aniline (2.5 hours). After completion, the reaction mixture was poured into ice cold water where the product precipitated as a cream coloured solid. Which was extracted into dry ether (3×25 mL) and the organic layer was dried over anhydrous Na$_2$SO$_4$ and concentrated under reduced pressure to afford the compound 26 (8.54 g, 96%) as a white coloured solid. The compound was subjected to analysis by NMR, IR spectroscopy and elemental analysis and compared with the reported product. Analysis as above.

6. Preparation of tert-butyl-4-chloro-2-(2, 2, 2-trifluoroacetyl) phenyl carbamate (Compound 27)

A 250 mL two neck round bottom flask equipped with mechanical stirrer and nitrogen inlet was charged with compound 26 (5 g, 23.6 mmol), THF (50 mL) and TMEDA (3.9 mL, 25.9 mmol). The resulting mixture stirred at ambient temperature until the total disappearance of solid. After that the temperature of reaction was brought down to −20° C. and then n-butyllithium (84.2 mL, 106 mmol) was added dropwise, the addition of n-butyllithium is an exothermic reaction so the temperature of the reaction was controlled by the rate of addition. After addition was completed, the reaction mixture was stirred at 0° C.-5° C. for 2 hours, the temperature of resulting mixture was again brought down to −15° C., at this temperature piperidine trifluoroacetic acid 67 (10.17 mL, 78.74 mmol) was added at once (addition of piperidine trifluoroacetic acid 67 at once, to avoid the formation of side products because of dimerization). The progress of the reaction was monitored by TLC (20% ethyl acetate in hexane) and GC. After completion of the reaction, the reaction mixture quenched with dropwise addition of previously cooled saturated ammonium chloride (25 mL), the organic layer was separated and washed with water (50 mL), brine solution (50 mL) and dried over anhydrous Na$_2$SO$_4$. The resulting organic layer evaporated by rotary evaporator to afford compound 27 (1.99 g, 28%); as yellow solid. TLC and GC of the obtained product indicated the presence of 10% starting material. The crude product was purified by flash column chromatography by using 60-120 mesh silica gel. The pure product was eluted with ethyl acetate and hexane (1:9) as the mobile phase. The appropriate fractions were combined and the solvent evaporated in vacuo to give the product. The purified compound was confirmed by FT-IR, $^1$H-NMR $^{13}$C-NMR spectroscopy and elemental analysis.

$^1$H-NMR-(400 MHz) in CDCl$_3$: δ 1.38 (s, 9H); 7.67 (d, 1H); 7.93 (s, 1H); 8.91 (d, J=9.24, 1H); 11.16 (brs, 1H). $^{13}$C-NMR in CDCl$_3$ (100 MHz): δ 27.4, 81.0, 116.7, 122.7, 127.8, 131.0, 137.5, 142.5, 182.5. $^{19}$FNMR in CDCl$_3$: δ −69.45. IR (cm$^{-1}$): 1093, 1247, 1411, 1636, 2972, 3374. Anal. calcd for C$_{13}$H$_{13}$ClF$_3$NO$_3$C, 48.24; H, 4.05; N, 4.33. Found: C, 48.15; H, 4.11; N, 4.36.

7. Preparation of tert-butyl-4-chloro-2-(4-cyclo propyl-1,1-trifluoro-2-hydroxy but-3-yn-2-yl) phenyl carbamate (compound 56)

The N-pyrrolidinylnorephedrine 60 (7.3 g, 35.75 mmol) was added in a round bottomed flask (with nitrogen inlet) which is previously charged with dry degassed THF (50 mL). The resulting mixture was cooled to −25° C. To this mixture, cyclopropyl acetylene 53 (3.55 mL, 35.78 mmol) and n-butyllithium (34.75 mL, 69.5 mmol) were added dropwise. After that, the reaction mixture temperature was raised to 0° C. and stirred for 30 min. Again the reaction mixture was cooled to −55° C., at this temperature compound 27 (5 g, 16.25 mmol) in dry THF (25 mL) under nitrogen was added to the reaction mixture. After addition, the resulting orange coloured solution was stirred for 1 hour at the same temperature. The reaction progress was monitored by TLC and GC, after completion the reaction was quenched with dropwise addition of 6N HCl and the final reaction mixture extracted with ethyl acetate (3×50 mL) and dried over anhydrous Na$_2$SO$_4$. The combined organic layers were evaporated to get the product as yellow color solid 56 (4.62 g, 84%). The chiral purity of the product was determined by using HPLC. A chiral column Cyclobond I 2000 was used as stationary phase and the methanol:water (80:20) as the mobile phase, flow rate 1 mL/min, DAD, which gave optimum detection at 252 nm. The final product was confirmed by FT-IR, $^1$H-NMR and $^{13}$C-NMR and elemental analysis.

$^1$H-NMR-(400 MHz) in CDCl$_3$: δ 0.74 (t, J=3.36, 2H); 0.83 (t, J=5.96, 2H); 1.21-1.55 (m, 1H) 4.17 (s, 1H); 7.25 (d, J=8.92, 1H); 7.61 (s, 1H); 8.30 (d, J=8.96, 1H); 9.41 (s, 1H). $^{13}$C-NMR in CDCl$_3$ (100 MHz): δ 0.003, 9.1, 14.1, 27.1, 70.1, 75.2, 94.2, 120.5, 121.3, 125.0, 128.9, 130.9, 177. $^{19}$FNMR in CDCl$_3$: δ −79.72 IR (cm$^{-1}$) 1262, 1360, 1487, 2235, 2794, 3330, 3419. Anal. calcd for C$_{13}$H$_{11}$ClF$_3$NO; C, 53.90; H, 3.83; N, 4.84; Found: C, 53.87; H, 3.89; N, 4.81.

Alternatively the reaction mixture was quenched by using saturated ammonium chloride and extracted with ethyl acetate, the combined organic layers were washed with brine solution and evaporated in vacuo to afford compound 51. The chiral purity of the product was determined by using HPLC. A chiral column Cyclobond I 2000 was used as stationary phase and the methanol:water (80:20) as the mobile phase, flow rate 1 mL/min, DAD, which gave optimum detection at 252 nm. And finally product was confirmed by FT-IR, $^1$H-NMR, $^{13}$C-NMR and elemental analysis.

$^1$H-NMR-(400 MHz) in CDCl$_3$: δ 0.74 (t, J=3.36, 2H); 0.83 (t, J=5.96, 2H); 1.14 (m, 9H); 1.21-1.55 (m, 1H); 4.17 (s, 1H); 7.25 (d, J=8.92, 1H); 7.61 (s, 1H); 8.30 (d, J=8.96, 1H); 9.41 (s, 1H). $^{13}$C-NMR in CDCl$_3$ (100 MHz): δ 0.003, 9.2, 14.7, 27.9, 70.5, 77.9, 85.7, 122.6, 124.3, 124.8, 128.8, 130.7, 137.4, 177.5. $^{19}$FNMR in CDCl$_3$: δ −79.72 IR (cm$^{-1}$) 1262, 1360, 1487, 2235, 2794, 3330, 3419. Anal. calcd for C$_{13}$H$_{11}$ClF$_3$NO; C, 59.76; H, 5.83; N, 4.27; Found: C, 59.77; H, 5.84; N, 4.27.

In the alternative embodiment compound 56 was prepared by using compound 53 from compound 26. N-Boc-4-Chloroaniline 26 (5 g, 21.27 mmol) was dissolved in THF (50 mL) and the resulting mixture was cooled to −55° C. and at this temperature n-butyllithium (42 mL, 106.3 mmol) was added slowly. The mixture was held at the same temperature for 1 hour. A mixture of compound 29 and 60 in dry THF (10 mL) was added to the above reaction and stirred for until completion of the reaction. The reaction progress was monitored by TLC and GC. After completion of the reaction, the reaction mixture quenched with dropwise addition of 6N HCl and the mixture was warmed to ambient temperature and extracted with MTBE. The combined organic layers dried over anhydrous Na$_2$SO$_4$ evaporated in vacuo, to afforded compound as yellow colour solid 56 (1.8 g, 47%). Analytically pure sample obtained by recrystallization with hexane. The chiral purity of the product was determined by using HPLC. A chiral column Cyclobond I 2000 was used as stationary phase and the methanol:water (80:20) as the mobile phase, flow rate 1 mL/min, DAD, which gave optimum detection at 252 nm. Finally the compound structure was confirmed by FT-IR, $^1$H-NMR, $^{13}$C-NMR and elemental analysis.

$^1$H-NMR-(400 MHz) in CDCl$_3$: δ 0.74 (t, J=3.36, 2H); 0.83 (t, J=5.96, 2H); 1.21-1.55 (m, 1H) 4.17 (s, 1H); 7.25 (d, J=8.92, 1H); 7.61 (s, 1H); 8.30 (d, J=8.96, 1H); 9.41 (s, 1H). $^{13}$C-NMR in CDCl$_3$ (100 MHz): δ 0.003, 9.1, 14.1, 27.1, 70.1, 75.2, 94.2, 120.5, 121.3, 125.0, 128.9, 130.9, 177. $^{19}$FNMR in CDCl$_3$: δ −79.72 IR (cm$^{-1}$) 1262, 1360, 1487, 2235, 2794, 3330, 3419. Anal. calcd for C$_{13}$H$_{11}$ClF$_3$NO; C, 53.90; H, 3.83; N, 4.84; Found: C, 53.87; H, 3.89; N, 4.81.

8. Preparation of 6-chloro-2-(4-cyclopropylethynyl)-4-(trifluoromethyl)-1H-benzo[d][1,3] oxazin-2-(4H)-one (efavirenz, compound 8)

(S)-Amino alcohol 56 (5 g, 17.3 mmol) was added to a round bottomed flask which was previously charged with the THF (50 mL), to this DBU (5.67 mL, 11.42 mmol) was added at room temperature. To this above stirred mixture diethyl carbonate 70 (7.5 mL, 19.38 mmol) was added and the mixture was further stirred at 60° C. for 2 hours. The completion of the reaction was monitored by TLC and GC. After completion, the reaction mixture was evaporated with rotary evaporator, diluted with water and extracted with ethyl acetate (3×50 mL). The combined organic layers were successively washed with aqueous hydrochloric acid, demineralized water and dried over anhydrous Na$_2$SO$_4$, concentrated in vacuo and purified on silica gel (60-120 mesh) column chromatography, the compound eluted with ethyl acetate and hexane (10:90) as mobile phase. Solvent evaporated to get the compound as white colored solid (5.8 g, 84.4%). The chiral purity of the product was determined by using HPLC. A chiral column Cyclobond I 2000 was used as stationary phase and the methanol:water (80:20) as the mobile phase, flow rate 1 mL/min, DAD, which gave optimum detection at 310 nm. Finally the structure of the compound was confirmed by FT-IR, $^1$H-NMR, $^{13}$C-NMR and elemental analysis.

$^1$H-NMR-(400 MHz) in CDCl$_3$: δ 0.85-0.96 (m, 4H); 1.38-1.45 (m, 1H); 6.85 (d, J=8.52, 1H); 7.39 (dd, J=8.52, 2.2 1H); 7.5 (s, 1H); 9.1 (s, 1H). 13C-NMR in CDCl$_3$ (100

MHz): δ 0.003, 9.4, 66.7, 77.9, 96.5, 116.8, 121.3, 124.1, 128.4, 133.8, 149.5, $^{19}$FNMR in CDCl$_3$: δ −80.9. IR (cm$^{-1}$) 1165, 1261, 1315, 1428, 1742, 2249, 3311. Anal. calcd for C$_{14}$H$_9$ClF$_3$NO$_2$; C, 53.27; H, 2.87; N, 4.44; Found C, 53.21; H, 2.89; N, 4.49.

Experimental Parameters and Analytical Data for Flow Synthesis Reactions

1. Preparation of tert-butyl-4-chloro phenyl carbamate Compound 26)

Preparation of tert-butyl-4-chloro phenyl carbamate (compound 26) in flow was done by using microreactor setup shown in FIG. 4. This microreactor setup was constructed by using Chemyx Fusion syringe pumps, 5 mL SGE glass syringes, and LTF reactor plates. Chemyx Fusion syringe pumps connected to four LTF microreactor plates via PTFE tubing, two of them are LTF-MX reactor plate which used for mixing the two reagents, another two are LTF-V reactor used for increasing the residence time.

Stock solution A was prepared by dissolving 4-chloroaniline 68 (5 g, 39.3 mmol) in THF (50 mL). Stock solution B was prepared by dissolving di-tert-butyl dicarbamate (9.13 mL, 43.3 mmol) in THF (50 mL). Stock solution C was prepared by dissolving sodium bicarbonate ((5 g, 78 mmol) in water (50 mL).

The stock solutions A, B and C were pumped into LTF microreactor plates using Chemyx Fusion syringe pumps and three 5 mL SGE glass syringes. These reactor plates were kept at a temperature of 30° C. and the samples collected at the end of the microreactor tubing were analyzed by using offline gas chromatography (GC). After completion, the reaction mixture extracted with ethyl acetate (3×50 mL), washed with water (50 mL) and brine solution (50 mL). The resulting organic layer dried over anhydrous Na$_2$SO$_4$ and evaporated under reduced pressure and finally compound analyzed by FT-IR, $^1$H-NMR $^{13}$C-NMR spectroscopy and elemental analysis. Based on the results of GC the reaction further scrutinized towards the optimization by investigating the effect residence time, concentration and temperature on conversion of 68.

1a. Effect of Residence Time on Conversion of Compound 68

4-Chloroaniline 68 (5 g, 39.3 mmol), di-tert-butyl dicarbamate (9.13 mL, 43.3 mmol) were dissolved in anhydrous, degassed tetrahydrofuran to a concentration of 0.78 M each and sodium bicarbonate (5 g, 78 mmol) was dissolved in water to a concentration of 1.1 M. These reagent solutions were fed into the microreactor at various residence times ranging from 0.35 min to 21 min into an LTF-MX reactor using three 5 mL SGE glass syringes, one syringe was filled with 4-chloroaniline 68, another one with aq. sodium bicarbonate and the last one with di-tert-butyl dicarbamate. To increase the residence time of the reaction, a residence plate reactor was added to the set up (LTF-V reactor). A sample was thereafter collected and analyzed by offline GC.

After collection of the sample, the reaction mixture washed with brine solution and dried over anhydrous Na$_2$SO$_4$. The resulting organic layer was evaporated under vacuum to afford white coloured solid as product which was used in step-2 without any purification, and finally characterized by using $^1$HNMR, $^{13}$CNMR, infrared spectroscopy and elemental analysis.

$^1$H-NMR (400 MHz) in CDCl$_3$: δ 1.22 (s, 9H); 7.33 (d, J=8.44, 2H); 7.69 (d, J=8.40, 2H): 9.31 (s, 1H). $^{13}$C-NMR in CDCl$_3$ (100 MHz): δ 27.6, 40.2, 81.0, 122.1, 127.1, 128.4, 138.8, 177.0. IR (cm$^{-1}$): 1172, 1368, 1475, 1652, 2872, 2910, 3290. Anal. calcd for C$_{11}$H$_{14}$ClNO$_2$: C, 58.03, H, 6.20, N, 6.15, Found: C, 58.08, H, 6.16, N, 6.11.

1b. Effect of Concentration of Di-Tert-Butyl Dicarbamate on Conversion of Compound 68

4-Chloroaniline 68 (5 g, 39.3 mmol), was dissolved in anhydrous, degassed tetrahydrofuran to a concentration of 0.78 M, sodium bicarbonate was dissolved in water to a concentration of 1.1 M and di-tert-butyl dicarbamate (9.13 mL, 43.3 mmol) was also dissolved in anhydrous, degassed tetrahydrofuran to get a concentration ranging from 0.70 M-0.98 M. These reagent solutions were fed into microreactor at various concentrations ranging from 0.93 M to 0.70 M of di-tert-butyl dicarbamate into an LTF-MX reactor using 5 mL SGE glass syringe, at a constant residence time (10.5 min) and temperature. One syringe was filled with 4-chloroaniline 68 another one with aqs sodium bicarbonate, third syringe was with di-tert-butyl dicarbamate. To increase the residence time of the reaction, a residence plate reactor was added to the set up (LTF-V reactor). A sample was thereafter collected at the end of the microreactor were analyzed by offline GC and the peak areas were used for calculating the % conversion of the product. After collection of the sample, the reaction mixture washed with brine solution and dried over anhydrous Na$_2$SO$_4$. The resulting organic layer was evaporated under vacuum to afford white coloured solid as product which was directly used in step-2 without any purification and finally characterized by using $^1$HNMR, $^{13}$CNMR, infrared spectroscopy and elemental analysis. Analysis as above.

1c. Effect of Temperature on Conversion of Compound 68

4-Chloroaniline 68 (5 g, 39.3 mmol), di-tert-butyl dicarbamate (9.13 mL, 43.3 mmol) was dissolved in anhydrous, degassed tetrahydrofuran to a concentration of 0.78 M each and sodium bicarbonate was dissolved in water to a concentration of 1.1 M. These reagent solutions were fed into an into microreactor using three 5 mL SGE glass syringes at various temperatures ranging from room temperature to 60° C. at constant residence time (10.5 min) and concentration, one syringe was filled with 4-chloroaniline 68 another one with aqs sodium bicarbonate and the third syringe was with di-tert-butyl dicarbamate. A sample was thereafter collected at the end of the microreactor were analyzed by offline GC and the peak areas were used for calculating the % conversion of the product. After collection of the sample, the reaction mixture washed with brine solution and dried over anhydrous Na$_2$SO$_4$. The resulting organic layer was evaporated under vacuum to afford white coloured solid as product which was used in step 2 without any purification and finally characterized by using $^1$HNMR, $^{13}$CNMR, infrared spectroscopy and elemental analysis. Analysis as above.

2. Preparation of tert-butyl-4-chloro-2-(2, 2, 2-trifluoroacetyl) phenyl carbamate (Compound 27)

Preparation of tert-butyl-4-chloro-2-(2,2,2-trifluoroacetyl) phenyl carbamate 27 in this thesis also called as trifluoro acetylation reaction. This reaction in flow was done by using microreactor. The microreactor setup was built using MR-Q pump, Chemyx Fusion syringe pumps, PTFE tubing, LTF reactor plates and quench columns. Quench columns were made using uniqsis glass column reactor with adjustable end fittings and which is filled with required amount of silica. Four LTF reactor plates (two LTF-MX reactor plate and two LTF-VS reactor plates) were used for this setup. These plates arranged in two beakers each beaker one mixing plate one residence plate and they marked as beaker 1 and beaker 2. MR-Q pump is used for pumping n-butyllithium, tert-butyl-4-chloro phenylcarbamate 26 and piperidine trifluoroacetic acid 67 in THF are pumped by using Chemyx Fusion syringe pumps. Two LTF-MX and two LTF-VS microreactor plates were used.

Stock solution A was prepared by dissolving tert-butyl-4-chloro phenyl carbamate 26 (5 g, 23.6 mmol) in THF (50 mL). Stock solution B was prepared by diluting 2.5 M of n-butyllithium (42.4 mL, 106.2 mmol) in dry degassed HPLC grade hexanes (50 mL). Stock solution C was prepared by dissolving piperidine trifluoroacetic acid 67 (10.17 mL, 78.74 mmol) in THF (50 mL).

The stock solution A was pumped into LTF microreactor plates with a MR-Q syringe pump, stock solution B was also pumped into same reactor plate with a Chemyx Fusion syringe pump and SGE glass syringe. In this microreactor plate, n-butyllithium reacts with compound 26 and generates dianion, which enters into LTF V microreactor plate, these two reactor plates kept at −75° C. and these plates are connected to another LTF MX microreactor plate where stock solution C enters into the plate with the help of other Chemyx Fusion syringe pump, the generated dianion in the first plate quenched with stock solution C. These reactor plates are kept at a temperature of −45° C. at the end microreactor plate connected to a quench column. Quench column made with silica to bind the piperidine by product. The sample collected at the end of the quench column was analyzed by using offline gas chromatography (GC). After conformation of reaction progress the solvent was evaporated in vacuo and the compound analyzed by FT-IR, $^1$H-NMR, $^{13}$C-NMR spectroscopy, and elemental analysis.

$^1$H-NMR-(400 MHz) in CDCl$_3$: δ 1.38 (s, 9H); 7.67 (d, 1H); 7.93 (s, 1H); 8.91 (d, 1H); 11.16 (brs, 1H). $^{13}$C-NMR in CDCl$_3$ (100 MHz): δ 27.4, 81.0, 116.7, 122.7, 127.8, 131.0, 137.5, 142.5, 182.5. $^{19}$FNMR in CDCl$_3$: δ −69.45. IR (cm$^{-1}$): 1093, 1247, 1411, 1636, 2972, 3374. Anal. calcd for $C_{13}H_{15}ClF_3NO_3C$, 48.24; H, 4.05; N, 4.33. Found: C, 48.15; H, 4.11; N, 4.36.

2a. Effect of Residence Time on Conversion of Compound 26

The tert-butyl-4-chloro phenyl carbamate 26 (5 g, 23.6 mmol) was dissolved in anhydrous degassed THF to a concentration of 0.1 M and n-butyllithium (2.5 M in hexanes from Sigma-Aldrich) was diluted to a concentration of 0.25 M in dry degassed hexanes and the trifluoro acetylating agent, piperidine trifluoroacetic acid 67 (10.17 mL, 78.74 mmol) was dissolved to a concentration of 0.14 M in a dry degassed THF. All the reagent solutions kept under the atmosphere of dry nitrogen. The temperature of the first beaker maintained at −45° C. and second beaker at −10° C. using dry ice. The quench column and the reactor loops were first flushed with anhydrous degassed solvent THF. The reagents were introduced into the reactor at different residence times ranging from 17.3 min-4.3 min by keeping the concentration of reagents and temperature constant. The tert-butyl-4-chloro phenyl carbamate 26 and piperidine trifluoroacetic acid 67 were introduced into the reactor with Chemyx Fusion syringe pumps and 10 mL SGE glass syringes, n-butyllithium fed into the reactor with a MR-Q syringe pump. Sample collected at the end of the microreactor were analyzed by offline GC and the % conversion was calculated by measuring peak areas. The product obtained after evaporation of solvent subjected to the $^1$HNMR, $^{13}$CNMR, IR and elemental analysis. Analysis as above.

2b. Effect of Concentration of n-Butyllithium on Conversion of Compound 26

The tert-butyl-4-chloro phenyl carbamate 26 (5 g, 23.6 mmol) was dissolved in anhydrous degassed THF to a concentration of 0.1 M and n-butyllithium (2.5 M in hexane from Sigma-Aldrich) was diluted to a concentrations from 0.5-0.25 M in dry degassed hexanes and the trifluoro acetylating agent, piperidine trifluoroacetic acid 67 (10.17 mL, 78.74 mmol) was dissolved to a concentration of 0.14 M in a dry degassed THF. All the reagent solutions kept under dry nitrogen. The temperature of the first beaker maintained at −45° C. and second beaker at −10° C. using dry ice. The quench column and the reactor loops were first flushed with anhydrous degassed solvent THF. The reagents were introduced into the reactor at constant residence time (8.6 min), temperature (beaker 1 at −45° C., beaker 2 at −10° C.) and by varying concentration of n-butyllithium from 0.5 M to 0.25 M. The tert-butyl-4-chloro phenyl carbamate 26 and piperidine trifluoroacetic acid 67 were introduced into the reactor with Chemyx Fusion syringe pumps and 10 mL SGE glass syringes, n-butyllithium fed into the reactor with a MR-Q syringe pump. A sample collected at the end of the microreactor was analyzed by offline GC and the % conversion was calculated by measuring peaks areas. The product obtained after evaporation of solvent subjected to the $^1$HNMR, $^{13}$CNMR, IR and elemental analysis. Analysis as above.

2c. Effect of Concentration of Trifluoro Acetylating Agent on Conversion of Compound 26

The tert-butyl-4-chloro phenyl carbamate 26 (5 g, 23.6 mmol) was dissolved in anhydrous degassed THF to a concentration of 0.1 M. n-butyllithium (2.5 M in hexanes from Sigma-Aldrich) was diluted to a concentration of 0.25 M in dry degassed hexane and the trifluoro acetylating agent, piperidine trifluoroacetic acid 67 (10.17 mL, 78.74 mmol) was dissolved to concentrations from 0.14-0.3 M in a dry degassed THF. All the reagent solutions kept under dry nitrogen. The temperature of the first beaker maintained at −45° C. and second beaker at −10° C. using dry ice. The quench column and the reactor loops were first flushed with anhydrous degassed solvent. The reagents were introduced into the reactor at constant residence time (8.6 min), temperature (beaker 1 at −45° C., beaker 2 at −10° C.) and at different concentrations of piperidine trifluoroacetic acid 67 ranging from 0.14 M-0.3 M. The tert-butyl-4-chloro phenyl carbamate 26 and piperidine trifluoroacetic acid 67 were introduced into the reactor with Chemyx Fusion syringe pumps and 10 mL SGE glass syringes, n-butyllithium fed into the reactor with a MR-Q syringe pump. A sample collected at the end of the microreactor was analyzed by offline GC and the % conversion was calculated by measuring peak areas. The product obtained after evaporation of solvent subjected to the $^1$HNMR, $^{13}$CNMR, IR and elemental analysis. Analysis as above.

2d. Investigating the Effect of Temperature on Conversion of Compound 26

The tert-butyl-4-chloro phenyl carbamate 26 (5 g, 23.6 mmol) was dissolved in anhydrous degassed THF to a concentration of 0.1 M. n-butyllithium (2.5 M in hexanes from Sigma-Aldrich) was diluted to a concentration of 0.25 M in dry degassed hexane and the trifluoro acetylating agent, piperidine trifluoroacetic acid 67 (10.17 mL, 78.74 mmol) was dissolved to a concentration of 0.14 M in a dry degassed THF. All the reagent solutions kept under dry nitrogen. The temperature of the beakers maintained at lower temperatures by using dry ice. The quench column and the reactor loops were first flushed with anhydrous degassed solvent. The reagents were introduced into the reactor at constant residence time (8.6 min), concentration and at different temperatures ranging from room temperature to −70° C. The tert-butyl-4-chloro phenyl carbamate 26 and piperidine trifluoroacetic acid 67 were introduced into the reactor with Chemyx Fusion syringe pumps and 10 mL SGE glass syringes, n-butyllithium fed into the reactor with a MR-Q syringe pump. A sample collected at the end of the microreactor was analyzed by offline GC and the % conversion was calculated by measuring peak areas. The product obtained after evaporation of solvent subjected to the $^1$HNMR, $^{13}$CNMR, IR and elemental analysis. Analysis as above.

3. Preparation of tert-butyl-4-chloro-2-(4-cyclo propyl-1,1-trifluoro-2-hydroxybut-3-yn-2-yl) phenyl carbamate (compound 56)

The reaction in flow was done by using microreactor setup comprising a MR-Q pump, Chemyx Syringe Pumps, PTFE tubing, and LTF reactor plates. Four LTF reactor plates (two LTF-MX reactor plate and two LTF-VS reactor plates) was used for this setup. These plates arranged in two beakers each beaker one mixing plate one residence plate and they marked as beaker 1 and beaker 2. The MR-Q pump was used for pumping n-butyllithium, N-pyrrolidinyl-norephedrine 60, cyclopropyl acetylene 53 and tert-butyl-4-chloro-2-(2,2,2-trifluoroacetyl) phenyl carbamate 27 in THF were pumped using Chemyx Fusion syringe pump as shown in FIG. 41.

Stock solution A was prepared by dissolving N-pyrrolidinylnorephedrine 60 (7.3 g, 35.75 mmol) and cyclopropyl acetylene 53 (3.35 mL, 35.78 mmol) in THF (50 mL). Stock solution B was prepared by diluting 2.5 M of n-butyllithium (26 mL, 41.25 mmol) in dry degassed HPLC grade hexanes (50 mL). Stock solution C was prepared by dissolving tert-butyl-4-chloro-2-(2,2,2-trifluoroacetyl) phenyl carbamate 27 (5 g, 16.25 mmol) in THF (50 mL).

The stock solution B was pumped into the LTF microreactor plates with the MR-Q syringe pump, stock solution A also pumped into same reactor plate with a Chemyx Fusion syringe pump and SGE glass syringe. In this microreactor plate n-butyllithium reacts with compound 60 & 53 and generates complex 74 which enters into LTF V microreactor plate, these two reactor plates kept at −45° C. and these plates are connected to another LTF MX microreactor plate where stock solution C enters into the plate with the help of another Chemyx Fusion syringe pump, the generated complex 74 in first plate attacks onto the compound 27 to get compound 56. These reactor plates were kept at a temperature of −45° C. at the end microreactor plate connected to a reservoir. The sample collected from the reservoir was analyzed using offline Gas chromatography (GC) and the peak areas were used for calculating % conversion. After conformation from GC the reaction mixture extracted with ethyl acetate (3×50 mL) and dried over anhydrous Na$_2$SO$_4$. The combined organic layers were evaporated to get the product. The structure of the compound was confirmed by FT-IR, $^1$H-NMR, $^{13}$C-NMR spectroscopy, and elemental analysis.

$^1$H-NMR-(400 MHz) in CDCl$_3$: δ 0.74 (t, J=3.36, 2H); 0.83 (t, J=5.96, 2H); 1.21-1.55 (m, 1H) 4.17 (s, 1H); 7.25 (d, J=8.92, 1H); 7.61 (s, 1H); 8.30 (d, J=8.96, 1H); 9.41 (s, 1H). $^{13}$C-NMR in CDCl$_3$ (100 MHz): δ 0.03, 9.1, 14.1, 27.1, 70.1, 75.2, 94.2, 120.5, 121.3, 125.0, 128.9, 130.9, 177. $^{19}$FNMR in CDCl$_3$: δ −79.72 IR (cm$^{-1}$) 1262, 1360, 1487, 2235, 2794, 3330, 3419. Anal. calcd for C$_{13}$H$_{11}$ClF$_3$NO; C, 53.90; H, 3.83; N, 4.84; Found: C, 53.87; H, 3.89; N, 4.81.

3a. Effect of Residence Time on the Conversion of Compound 27

The tert-butyl-4-chloro-2-(2,2,2-trifluoroacetyl) phenyl carbamate 27 (5 g, 16.25 mmol) was dissolved in anhydrous degassed THF to a concentration of 0.35 M. n-Butyllithium (2.5 M in hexane from Sigma-Aldrich) was diluted to a concentration of 0.45 M in dry degassed hexane and N-pyrrolidinylnorephedrine 60 (7.3 g, 35.75 mmol), cyclopropyl acetylene 53 (3.55 mL, 35.78 mmol) were dissolved in THF to a concentration of 0.45 M. All the reagent solutions kept under dry nitrogen. The temperature of the first beaker was maintained at −45° C. and second beaker at −10° C. using dry ice. The reagents were introduced into the reactor at different residence times ranging from 8.6 min to 1.7 min by keeping the concentration of reagents and temperature constant. A sample collected at the end of the microreactor was analyzed by offline GC and the % conversion was calculated by measuring peaks areas. The product obtained from the reaction analyzed by $^1$HNMR, $^{13}$CNMR, IR and elemental analysis. Analysis as above.

3b. Effect of Concentration of n-Butyllithium on the Conversion of Compound 27

The tert-butyl-4-chloro-2-(2,2,2-trifluoroacetyl) phenyl carbamate 27 (5 g, 16.25 mmol) was dissolved in anhydrous degassed THF to a concentration of 0.35 M. n-Butyllithium (2.5 M in hexane from Sigma-Aldrich) was diluted to a concentrations ranging from 0.25 M-0.45 M in dry degassed hexane and N-pyrrolidinylnorephedrine 60 (7.3 g, 35.75 mmol), cyclopropyl acetylene 53 (3.55 mL, 35.78 mmol) were dissolved in THF to a concentration of 0.45 M. All the reagent solutions kept under dry nitrogen. The temperature of first beaker was maintained at −45° C. and second beaker at −10° C. using dry ice. The reagents were introduced into the reactor at constant residence time (4.3 min), temperature (beaker 1 at −45° C., beaker 2 at −10° C.) and by varying concentration of n-butyllithium from 0.27 M to 0.45 M. A sample collected at the end of the microreactor was analyzed by offline GC and the % conversion was calculated by measuring peaks areas. The product obtained from the reaction after purification was subjected to $^1$H NMR, $^{13}$C NMR, IR and elemental analysis. Analysis as above.

3c. Investigating the Effect of Concentration of Cyclopropyl Acetylene on the Conversion of Compound 27

The tert-butyl-4-chloro-2-(2,2,2-trifluoroacetyl) phenyl carbamate 27 (5 g, 16.25 mmol) was dissolved in anhydrous degassed THF to a concentration of 0.35 M. n-Butyllithium (2.5 M in hexane from Sigma-Aldrich) was diluted to a concentration 0.45 M in dry degassed hexane and N-pyrrolidinylnorephedrine 60 (7.3 g, 35.75 mmol), cyclopropyl acetylene 53 (3.55 mL, 35.78 mmol) were dissolved in THF to concentrations ranging from 0.5 M-0.65 M. All the reagent solutions kept under dry nitrogen. The temperature of the first beaker was maintained at −45° C. and second beaker at −10° C. using dry ice. The quench column and the reactor loops were first flushed with anhydrous degassed solvent. The reagents were introduced into the reactor at constant residence time (4.3 min), temperature (beaker 1 at −45° C., beaker 2 at −10° C.) and at different concentrations of cyclopropyl acetylene 53 ranging from 0.5 M-0.65 M. A sample collected at the end of the microreactor was analyzed by offline GC and the % conversion was calculated by measuring peaks areas. The product obtained from the reaction after purification subjected to $^1$H NMR, $^{13}$C NMR, IR and elemental analysis. Analysis as above.

3d. Investigating the Effect of Temperature on the Conversion of Compound 27

The tert-butyl-4-chloro-2-(2 2,2-trifluoroacetyl) phenyl carbamate 27 (5 g, 16.25 mmol) was dissolved in anhydrous degassed THF to a concentration of 0.35M. n-Butyllithium (2.5 M in hexane from Sigma-Aldrich) was diluted to a concentration of 0.45 M in dry degassed hexane and N-pyrrolidinylnorephedrine 60 (7.3 g, 35.75 mmol), cyclopropyl acetylene 53 (3.55 mL, 35.78 mmol) were dissolved in THF to a concentration of 0.5 M. All the reagent solutions kept under dry nitrogen. The temperatures of the beakers maintained at lower temperatures by using dry ice. The reagents were introduced into the reactor at constant residence time (4.3 min), concentration and at different temperatures ranging from room temperature to −70° C. A sample collected at the end of the microreactor was analyzed by offline GC and the % conversion was calculated by measuring peaks areas. The product obtained from the reaction after purification subjected to $^1$H NMR, $^{13}$C NMR, IR and elemental analysis. Analysis as above.

4. Preparation of (S)-6-chloro-(cyclopropylethynyl)-1,4-dihydro-4-(trifluoromethyl)-2H-3,1-benzoxazin-2-one 8

This reaction in flow was done by using a microreactor setup comprising two Chemyx Fusion syringe pumps, three SGE glass syringes, PTFE tubing and four LTF microreactors. The LTF microreactors were arranged in two beakers, each beaker accommodated with one mixing plate (LTF-MX microreactor) and one residence plate (LTF-MS microreactor). The Chemyx Fusion syringe pumps were connected to the LTF microreactors through PTFE tubing.

Stock solution A was prepared by dissolving (S)-amino alcohol 56 (5 g, 17.3 mmol) in THF (50 mL). Stock solution B was prepared by dissolving 1,8-diazabicyclo[5.4.0]undec-7-ene (5.67 mL, 11.42 mmol) in THF (50 mL). Stock solution C was prepared by dissolving diethyl carbonate (7.5 mL, 19.38 mmol) in THF (50 mL).

The stock solutions A & B were pumped into the LTF microreactor plates with a Chemyx Fusion syringe pump and SGE glass syringes where, after mixing it enters into another set of microreactor plates, where stock solution C enters into the plate with the help of another Chemyx Fusion syringe pump. The cyclisation occurs in this microreactor plate. The second set of microreactor plates were kept at a temperature of 60° C. End of the microreactor connected to a back pressure regulator and to a reservoir. The sample collected from the reservoir was analyzed by using offline Gas chromatography (GC). The organic layers collected at the end of reactor were washed with aqueous hydrochloric acid, demineralized water and dried over anhydrous $Na_2SO_4$, concentrated in vacuo and purified on silica gel (60-120 mesh) column chromatography, the compound eluted with ethyl acetate and hexane (10:90) as mobile phase. Solvent evaporated to get the compound as white coloured solid. The structure of the compound was confirmed by FT-IR, $^1$H-NMR, $^{13}$C-NMR and elemental analysis.

$^1$H-NMR-(400 MHz) in $CDCl_3$: δ 0.85-0.96 (m, 4H); 1.38-1.45 (m, 1H); 6.85 (d, J=8.52, 1H); 7.39 (dd, J=8.52, 2.2 1H); 7.5 (s, 1H); 9.1 (s, 1H). 13C-NMR in $CDCl_3$ (100 MHz): δ 0.003, 9.4, 66.7, 77.9, 96.5, 116.8, 121.3, 124.1, 128.4, 133.8, 149.5, $^{19}$FNMR in $CDCl_3$: δ −80.9. IR ($cm^{-1}$) 1165, 1261, 1315, 1428, 1742, 2249, 3311. Anal. calcd for $C_{14}H_9ClF_3NO_2$; C, 53.27; H, 2.87; N, 4.44; Found C, 53.21; H, 2.89; N, 4.49.

4a. Investigating the Effect of Residence Time on the Conversion of Compound 56

(S)-Amino alcohol 56 (5 g, 17.3 mmol) was dissolved in anhydrous THF to a concentration of 0.60 M, 1,8-diazabicyclo[5.4.0]undec-7-ene (5.67 mL, 11.42 mmol) was dissolved in anhydrous THF to a concentration of 0.40 M and diethyl carbonate (7.5 mL, 19.38 mmol) was dissolved in anhydrous THF to a concentration of 0.70 M. The temperatures of the first beaker was maintained at room temperature and second beaker at 60° C. The reagents were introduced into the reactor at various residence times ranging from 17.3 min-0.43 min, at constant concentration and temperature. A sample was collected at the end of the microreactor and was analyzed by offline GC and the % conversion was calculated by measuring peaks areas. The product obtained from the reaction analyzed by $^1$H-NMR, $^{13}$C-NMR, IR and elemental analysis. Analysis as above.

4b. Investigating the Effect of Temperature on the Conversion of Compound 56

(S)-Amino alcohol 56 (5 g, 17.3 mmol) was dissolved in anhydrous THF to a concentration of 0.60 M, 1,8-diazabicyclo[5.4.0]undec-7-ene (5.67 mL, 11.42 mmol) was dissolved in anhydrous THF to a concentration of 0.40 M and diethyl carbonate (7.5 mL, 19.38 mmol) was dissolved in anhydrous THF to a concentration of 0.70 M. The reagents were introduced into the at constant residence time (2.4 min), concentration and at different temperatures of beaker 2 ranging from room temperature to 120° C. while keeping the beaker 1 temperature constant. A sample collected at the end of the microreactor was analyzed by offline GC and the % conversion was calculated by measuring peaks areas. The product obtained from the reaction analyzed by $^1$H-NMR, $^{13}$C-NMR, IR and elemental analysis. Analysis as above.

4c. Investigating the Effect of Concentration on the Conversion of Compound 56

(S)-Amino alcohol 56 (5 g, 17.3 mmol) was dissolved in anhydrous THF to a concentration of 0.60 M, 1,8-diazabicyclo[5.4.0]undec-7-ene (5.67 mL, 11.42 mmol) was dissolved in anhydrous THF to a concentration of 0.40 M and diethyl carbonate (7.5 mL, 19.38 mmol) was dissolved in anhydrous THF to get a concentrations ranging from 0.40 M-1 M. The reagents were introduced into the reactor at constant residence time (2.4 min), temperature and at different concentrations ranging from 0.40 M-1 M. A sample collected at the end of the microreactor was analyzed by offline GC and the % conversion was calculated by measuring peaks areas. The product obtained from the reaction analyzed by $^1$H-NMR, $^{13}$C-NMR, IR and elemental analysis.

Analysis as above.

This above description of some of the illustrative embodiments of the invention is to indicate how the invention can be made and carried out. Those of ordinary skill in the art will know that various details may be modified thereby arriving at further embodiments, but that many of these embodiments will remain within the scope of the invention.

The invention claimed is:

1. A method for the manufacture of (S)-6-chloro-(cyclopropylethynyl)-1,4-dihydro-4-(trifluoromethyl)-2H-3,1-benzoxazin-2-one of formula 8

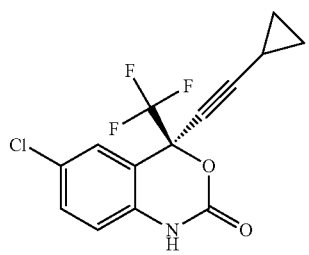

comprising the steps of:
a) preparing tert-butyl-4-chloro phenyl carbamate of formula 26

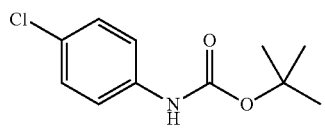

by reacting 4-chloroaniline with di-tert-butyl dicarbamate,
b) reacting the tert-butyl-4-chloro phenyl carbamate of formula 26 with butyllithium and piperidine trifluoroacetic acid of formula 67

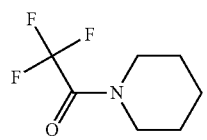

in a trifluroacetylation reaction to produce tert-butyl-4-chloro-2-(2,2,2-trifluoroacetyl) phenyl carbamate of formula 27

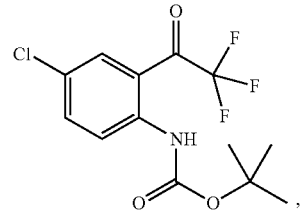

c) reacting the compound of formula 27 with cyclopropyl acetylene of formula 53 and (1R,2S) N-pyrrolidinylnorephedrine of formula 60

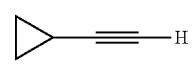

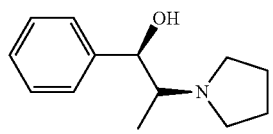

in the presence of butyllithium to produce (S)-2-(2-amino-5-chlorophenyl)-4-cyclopropyl-1,1,1-trifluoro-3-butyn-2-ol of formula 56

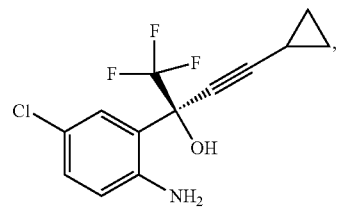

d) reacting the compound of formula 56 with a compound of the formula 70

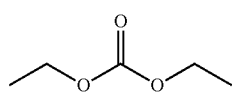

in the presence of 1,8-diazabicyclo[5.4.0]undec-7-ene to produce (S)-6-chloro-(cyclopropylethynyl)-1,4-dihydro-4-(trifluoromethyl)-2H-3,1-benzoxazin-2-one of formula 8,
wherein the method is a flow synthesis method.

2. The method according to claim 1, wherein in step (b) or step (c) the butyllithium is n-butyllithium.

3. The method according to claim 1, wherein in step (b) the reaction is performed in the presence of tetramethylethylenediamine.

4. The method according to claim 1, wherein the reactions of steps (a)-(d) are each independently performed in a solvent or solvent mixture selected from the group consisting of tetrahyroduran, dichloromethane, acetonitrile, acetone, water, and mixtures thereof.

5. The method according to claim 1, further comprising recrystallization from a solution of ethyl acetate in heptane.

6. A method for the manufacture of (S)-6-chloro-(cyclopropylethynyl)-1,4-dihydro-4-(trifluoromethyl)-2H-3,1-benzoxazin-2-one of formula 8

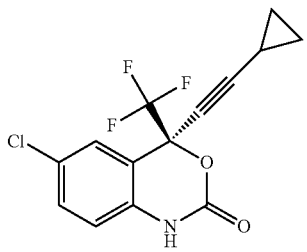

8 comprising the steps of:
a) preparing tert-butyl-4-chloro phenyl carbamate of formula 26

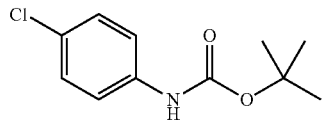

26 by reacting 4-chloroaniline with di-tert-butyl dicarbamate,
b) reacting the tert-butyl-4-chloro phenyl carbamate of formula 26 with cyclopropylethynyl trifluoromethyl ketone of formula 29 and (1R,2S) N-pyrrolidinyl-norephedrine of formula 60

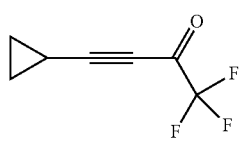

29

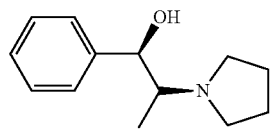

60 in the presence of butyllithium to produce (S)-2-(2-amino-5-chlorophenyl)-4-cyclopropyl-1,1,1-trifluoro-3-butyn-2-ol of formula 56

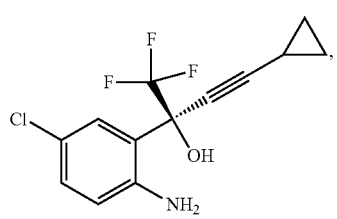

56 c) reacting the compound of formula 56 with a compound of the formula 70

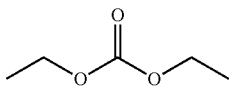

70 in the presence of 1,8-diazabicyclo[5.4.0]undec-7-ene to produce (S)-6-chloro-(cyclopropylethynyl)-1,4-dihydro-4-(trifluoromethyl)-2H-3,1-benzoxazin-2-one of formula 8,
wherein the method is a flow synthesis method.

7. The method according to claim 6, wherein in step (b) the butyllithium is n-butyllithium.

8. The method according to claim 6, wherein the reactions of steps (a)-(c) are each independently performed in a solvent or solvent mixture selected from the group consisting of tetrahyroduran, dichloromethane, acetonitrile, acetone, water, and mixtures thereof.

9. The method according to claim 6, further comprising recrystallization from a solution of ethyl acetate in heptane.

10. The method of claim 6, wherein the reaction of step (a) has a residence time of between about 5 minutes and about 12 minutes.

11. The method of claim 6, wherein in step (a) the molar ratio of 4-chloroaniline to di-tert-butyl dicarbamate is in the range of about 1:1 to 1:1.2.

12. The method of claim 6, wherein the reaction of step (a) is performed at a temperature of about 30° C. to about 60° C.

13. The method of claim 1, wherein the reaction of step (b) is performed at a temperature of about −60° C. to about −40° C.

14. The method of claim 1, wherein the reaction of step (b) has a residence time of between about 5 minutes and about 12 minutes.

15. The method of claim 1, wherein in step (c) the molar ratio of tert-butyl-4-chloro-2-(2,2,2-trifluoroacetyl) phenyl carbamate of formula 27 to cyclopropyl acetylene of formula 53 is in the range of about 1:1.2 to 1:1.4.

16. The method of claim 6, wherein the reaction of step (d) or (c) respectively has a residence time of between about 2 minutes and about 10 minutes.

17. The method of claim 6, wherein the reaction of step (d) or (c) respectively is performed at a temperature of about 80° C. to 120° C.

18. The method of claim 6, wherein in step (d) or (c) respectively the molar ratio of (S)-2-(2-amino-5-chlorophenyl)-4-cyclopropyl-1,1,1-trifluoro-3-butyn-2-ol of formula 56 to compound of the formula 70 is in the range of about 1:1.1 to 1:1.4.

19. The method of claim 1, wherein the reaction of step (a) has a residence time of between about 5 minutes and about 12 minutes.

20. The method of claim 1, wherein in step (a) the molar ratio of 4-chloroaniline to di-tert-butyl dicarbamate is in the range of about 1:1 to 1:1.2.

21. The method of claim 1, wherein the reaction of step (a) is performed at a temperature of about 30° C. to about 60° C.

22. The method of claim 1, wherein in step (c) the molar ratio of tert-butyl-4-chloro-2-(2,2,2-trifluoroacetyl) phenyl carbamate of formula 27 to cyclopropyl acetylene of formula 53 is in the range of about 1:1.2 to 1:1.4.

23. The method of claim 1, wherein the reaction of step (d) or (c) respectively has a residence time of between about 2 minutes and about 10 minutes.

24. The method of claim 1, wherein the reaction of step (d) or (c) respectively is performed at a temperature of about 80° C. to 120° C.

25. The method of claim 1, wherein in step (d) or (c) respectively the molar ratio of (S)-2-(2-amino-5-chlorophenyl)-4-cyclopropyl-1,1,1-trifluoro-3-butyn-2-ol of formula 56 to compound of the formula 70 is in the range of about 1:1.1 to 1:1.4.

* * * * *